(12) United States Patent
Zhang et al.

(10) Patent No.: US 6,905,873 B1
(45) Date of Patent: Jun. 14, 2005

(54) RECOMBINANT P53 ADENOVIRUS METHODS AND COMPOSITIONS

(75) Inventors: Wei-Wei Zhang, Sugar Land, TX (US); Jack A Roth, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 08/626,678

(22) Filed: Apr. 2, 1996

Related U.S. Application Data

(63) Continuation of application No. 08/145,826, filed on Oct. 29, 1993, now Pat. No. 6,410,010, which is a continuation-in-part of application No. 07/960,513, filed on Oct. 13, 1992, now Pat. No. 6,017,524.

(51) Int. Cl.$^7$ .................. C12N 15/861; C12N 15/63
(52) U.S. Cl. ................. 435/320.1; 435/235.1; 435/69.1; 435/45.5; 435/456; 435/325; 435/366; 424/93.1; 424/93.2; 424/93.6
(58) Field of Search .................. 435/320.1, 235.1, 435/69.1, 455, 456, 325, 366, 240.2; 424/93.1, 93.2, 93.6

(56) References Cited

U.S. PATENT DOCUMENTS

| | | | |
|---|---|---|---|
| 4,740,463 A | 4/1988 | Weinberg et al. | |
| 4,920,209 A | 4/1990 | Davis et al. | |
| 4,980,289 A | 12/1990 | Temin et al. | |
| 5,055,400 A | 10/1991 | Lo et al. | |
| 5,252,479 A | * 10/1993 | Srivastava | 435/235.1 |
| 5,362,623 A | 11/1994 | Vogelstein et al. | 435/6 |
| 5,527,676 A | 6/1996 | Vogelstein et al. | 435/6 |
| 5,532,220 A | 7/1996 | Lee et al. | |
| 5,932,210 A | 8/1999 | Gregory et al. | 424/93.2 |
| 6,143,290 A | 11/2000 | Zhang et al. | |
| 6,410,010 B1 | 6/2002 | Zhang et al. | |
| 6,511,847 B1 | 1/2003 | Zhang et al. | |
| 6,677,312 B1 | 1/2004 | Vogelstein et al. | 514/44 |

FOREIGN PATENT DOCUMENTS

| | | |
|---|---|---|
| EP | 0174608 | 9/1985 |
| EP | 0351585 | 6/1989 |
| EP | 0 390 323 | 10/1990 |
| EP | 0475623 | 8/1991 |
| FR | 2688514 | 9/1993 |
| JP | 04-009338 | 1/1992 |
| JP | 8-508879 | 9/1996 |
| WO | WO 91/05180 | 5/1990 |
| WO | WO 90/10448 | 9/1990 |
| WO | WO 91/15580 | 10/1991 |
| WO | WO 93/03769 | 3/1993 |
| WO | WO 93/19191 | 9/1993 |
| WO | WO 93 25224 | 12/1993 |
| WO | WO 94 06910 | 3/1994 |
| WO | WO 94/08026 | 4/1994 |
| WO | WO 94/10323 | 5/1994 |
| WO | WO 94/18992 | 9/1994 |
| WO | WO 94/26914 | 11/1994 |
| WO | WO 95/02697 | 1/1995 |
| WO | WO 95/11301 | 4/1995 |
| WO | 95 11984 | 5/1995 |
| WO | WO 95/14101 | 5/1995 |
| WO | WO 95/14102 | 5/1995 |
| WO | WO 95/23867 | 9/1995 |
| WO | WO 95 30002 | 11/1995 |
| WO | WO 94/24297 | 10/1997 |

OTHER PUBLICATIONS

Berkner, Current Topics in Microbiology and Immunology, 1992, vol. 158, pp. 39–66.*

Kaufman, Methods in Enzymology, 1990, vol. 185, pp. 487–511.*

Bacchetti et al., International Journal of Oncology, vol. 3 pp. 781–788, Oct. 22, 1993.*

Casey, G., et al., "Growth Suppression of Human Breast Cancer Cells by the Introduction of a Wild–Type p53 Gene," *Oncogene*, 6(10) :1791–1797.

Gomez–Foix, A., et al., "Adenovirus–mediated Transfer of the Muscle Glycogen Phosphorylase Gene into Hepatocytes Confers Altered Regulation of Glycogen Metabolism," *The Journal of Biological Chemistry*, 267 (35) :25129–25134, 1992.

Hollstein, M., et al., "p53 Mutations in Human Cancers," *Science*, 253:49–53, 1991.

Jaffe, H.A., et al., "Adenovirus–mediated in vivo Gene Transfer and Expression in Normal Rat Liver," *Nature Genetics*, 1:372–378, 1992.

Le Gal La Salle, G., et al., "An Adenovirus Vector for Gene Transfer into Neurons and Glia in the Brain," *Science*, 259:988–990, 1993.

Mercer, W. Edward, "Cell Cycle Regulation and the p53 Tumor Suppressor Protein." *Critical Reviews in Eukaryotic Gene Expression*, 2(3) :251–263, 1992.

Montenarh, M., "Biochemical, Immunological, and Functional Aspects of the Growth–Suppressor/Oncoprotein p53," *Critical Reviews in Oncogenesis*, (3) :233–256, 1992.

Prevec, L., et al. "Use of Human Adenovirus–based Vectors for Antigen Expression in Animals," *J. Gen. Virol.*, 70:429–434, 1989.

(Continued)

Primary Examiner—David Guzo
(74) Attorney, Agent, or Firm—Fulbright & Jaworski L.L.P.

(57) ABSTRACT

Described are simplified and efficient methods for preparing recombinant adenovirus using liposome-mediated cotransfection and the direct observation of a cytopathic effect (CPE) in the transfected cells. Also disclosed are compositions and methods involving novel p53 adenovirus constructs, including methods for restoring p53 function and tumor suppression in cells and animals having abnormal p53.

13 Claims, 12 Drawing Sheets

OTHER PUBLICATIONS

Rosenfeld, M., et al., "Adenovirus–Mediated Transfer of a Recombinant α1–Antitrypsin Gene to the Lung Epithelium in Vivo," *Science*, 252:431–434, 1991.

Rosenfeld, M., et al., "In Vivo Transfer of the Human Cystic Fibrosis Transmembrane Conductance Regulator Gene to the Airway Epithelium," *Cell*, 68:143–155, 1992.

Stratford–Perricaudet, L., "Evaluation of the Transfer and Expression in Mice of an Enzyme–Encoding Gene Using a Human Adenovirus Vector," *Human Gene Therapy*, 1:241–256, 1990.

Stratford–Perricaudet, L., "Gene Transfer Into Animals: the Promise of Adenovirus," *Human Gene Transfer*, 219:51–61, 1991.

Stratford–Perricaudet, L., "Feasibility of Adenovirus–Mediated Gene Transfer in vivo," *Bone Marrow Transplantation*, 9 (Suppl.1) :151–152, 1992.

Stratford–Perricaudet, L., "Widespread Long–term Gene Transfer to Mouse Skeletal Muscles and Heart," *J. Clin. Invest.*, 90:626–630, 1992.

Weinberg, R., "Tumor Suppressor Genes," *Science*, 254:1138–1146, 1991.

Zhang & Roth, "Propagation of Recombinant p53 Adenovirus and Evaluation of its Effect on Human Lung Cancer Cell Lines," *The Fourth Meeting on the Molecular Basis of Cancer*, Jun. 1993.

Co–pending U.S. patent application No. 08/459,713.

Co–pending U.S. patent application No. 09/413,109.

Co–pending U.S. patent application No. 09/447,681.

Co–pending U.S. patent application No. 10/180,895.

Felgner et al., "Lipfection: a highly efficient, lipid–mediated DNA–transfection procedure," *Proc. Natl. Acad. Sci. USA*, 84:7413–7417, 1987.

Gjerset et al., "Dominant Effect of Transduced Wild–type p53 over endogenous mutant p53 in sensitizing tumor cells to therapy," *Proceedings of the Am. Assoc. for Cancer Res.*, 36:21, 1995. (Abstract 123).

Eaves et al., "The biology of normal and neoplatic stem cells in CML," Chronic Myeloid Leukemia, $2^{nd}$ Int'l Conference, Bologma, Italy, Oct. 4–7, 1992. From *Leukemia and Lymphoma*, 11:245–253 (1993).

Gomez–Navarro et al., "Gene Therapy for Cancer," *European Journal of Cancer*, 35:867–885, 1999.

Green, "When the Products of Oncogenes and Anti–Oncogenes Meet," *Cell*, 56:1–3, 1989.

Harper et al., "the p21 cdk–interacting protein cip1 is a potent inhibitor of g1 cyclin–dependent kinases," *Cell*, 75:805–816, 1993.

Huber et al., "Retroviral–Mediated Gene Therapy for the Treatment of Hepatocellular Carcinoma: An Innovative Approach for Cancer Therapy," *Proc. Natl. Acad. Sci Usa*, 88:8039–8043, 1991.

In: Comprehensive Textbook of Oncology, vol. 1, 2nd.Ed., Williams & Wilkins, Publ., pp. 477, 527–536, 565–568, 590–594, 607–612, 1986.

In: Comprehensive Textbook of Oncology, vol. 2, 2nd. Ed., Williams & Wilkins, Publ., pp. 1098, 1138–1140, 1170, 1329, 1368, 1569–1572, 1986.

Kastan "p53 and other molecular controls of the response to DNA damage." *Adv. Exp. Med. Biol.*, 339:295–296, 1993.

Klinken et al., "Transcriptional and Post–Transcriptional Regulation of C–MYC C–MYB and p53 During Proliferation and Differentiation of Muring Erythroleukemia Cells Treated with DFMO and DMSO," *Exp. Cell Res.*, 178:185–198, 1988.

Kriegler et al., In: Gene Transfer and Expression: a laboratory manual, 1990.

Lord et al., "Macrophage Inflammatory Protein: Its Characteristics, Biological Properties and Role in the Regulation of Haemopoiesis," *International J. of Hemaiology*, 57:197–206, 1993.

Marx, "Cell Death Studies Yield Cancer Clues," *Science*, 259:760–761 (1993).

Muzyczka, "Use of adeno–assiiated virus as a general transduction vector for mammalian cells," *Microbiol. Immunol.*, 158:98–129, 1992.

Orazi et al., "Frequent p53 overspression in therapy related mylodysplastic syndromes and acute myeloid leukemias: an immunohistochemical study of bone marrow biopaies," *Mod. Path.*, 6:521–525, 1993.

Ryan et al., "Cell Cycle Analysis of p53–Induced cell Death in Murine Erythroleukemia Cells," *Mol. Cell. Biol.*, 13:711–719, 1993.

Singleton and Sainsbury, Dictionary of Microbiology and Molecular Biology, 2nd Ed., John Wiley & Sons, Publ., pp. 591 and 920, 1987.

Stedman's Medical Dictionary, 25th Ed., Wiliams & Wilkins, Publ., p.245, 1990.

Stratagene catalogue, p. 39, 1988.

Fan et al., "p53 gene mutations are associated with decreased sensitivity of human lymphoma cells to DNA damaging agents," *Cancer Res.*, 54(22):5824–5830, 1994.

Fujiwara et al., "Induction of chemosensitivity in human lung cancer cells in vivo by adenovirus–mediated transfer of the wild–type p53 gene," *Surgical Forum*, 45:524–526, 1994.

Bacchetti and Graham, "Inhibition of Cell Proliferation by an Adenovirus Vector Expressing the Human Wild Type p53 Protein." *Int'l J Oncology*, 3(5):781–788. Nov. 1993.

Santhanam et al., "Repression of the interleukin 6 gene promoter by p53 and the retinoblastoma susceptibility gene product." *Proc. Natl. Acad. Sci. USA*, 88:7605–7609, 1991.

Bandyopadhyay and Temin, "Expression of Complete Chicken Thymidine Kinase Gene Inserted in a Tetrovirus Vector," *Molecular and Cellular Biology*, 4(4):749–754, 1984.

Bowtell et al., "Comparison of Expression in Hemopoietic Cells by Retroviral Vectors Carrying Two Genes," *Journal of Virology*, 62(7):2464–2473, 1988.

Casson et al., "p53 Gene Mutations in Barrett's Epithelium and Esophageal Cancer," *Cancer Research*, 51:4495–4499, 1991.

Chen et al., "Genetic Mechanisms of Tumor Suppression by the Human p53 Gene," *Science*, 250:1576–1580, 1990.

Chen et al., "Expression of Wild–Type p53 in Human A673 Cells Suppresses Tumorigenicity but Not Growth Rate," *Oncogene*, 6:1799–1805, 1991.

Goyette et al., "Progression of Colorectal Cancer is Associated with Multiple Tumor Suppressor Gene Defects but Inhibition of Tumorigenicity is Accomplished by Correction of Any Single Defect via Chromosome Transfer," *Molecular and Cellular Biology*, 12(3):1387–1395, 1992.

Gusterson et al., "Expression of p53 in Premalignant and Malignant Squamous Epithelium," *Oncogene*, 6:1785–1798, 1991.

Kumar et al., "Activation of ras Oncogenes Preceding the Onset of Neoplasia," *Science*, 248:1101–1104, 1990.

Maxwell et al., "Inefficiency of Expression of Luciferase Reporter from Transfected Murine Leukaemia Proviral DNA May Be Partially Overcome by Providing a Strong Polyadenylation Signal," *Journal of General Virology*, 72:1721–1724, 1991.

Mukhopadhyay et al., "Specific Inhibition of K–ras Expression and Tumorigenicity of Lung Cancer Cells by Antisense RNA," *Cancer Research*, 51:1744–1748, 1991.

Owens and Boyd, "Expressing Antisense Po RNA in Schwann Cells Perturbs Myelinatino," *Development*, 112:639–649, 1991.

Palmer et al., "Efficient Retrovirus–Mediated Transfer and Expression of Human Adenosine Deaminase Gene in Diploid Skin Fibroblasts from an Adenosine Deaminase–Deficient Human," *Proceedings of the National Academy of Science USA*, 84:1055–1059, 1987.

Seyama et al., "In Vitro and In Vivo Regulation of Liver Epithelial Cells Carrying a Metallothionein–rasT24 Fusion Gene," *Molecular Carcinogenesis*, 1:89–95, 1988.

Takahashi et al., "Wild–Type but Not Mutant p53 Suppresses the Growth of Human Lung Cancer Cells Bearing Multiple Genetic Lesions," *Cancer Research*, 52:2340–2343, 1992.

Zhou and Duesberg, "*myc* Protooncogene Linked to Retroviral Promoter, but Not the Enhancer, Transforms Embryo Cells," *Proceedings of the National Academy of Science USA*, 85:2924–2928, 1988.

Conry, "New Gene Therapy Cleared for Use Against Lung Cancer," *Biotech Daily*, pp. 3–4, Sep. 18, 1992.

Sundaresan et al., "Somatic Genetic Changes in Pre–Invasive Lesions in Bronchial Epithelium," *J. Pathol.*, 167 (Suppl) 1992, 100A, Abstract Only.

Debus et al., *J. Cancer Res. Clin. Oncol.*, 116(Suppl Part 1):5–162, Abstract #A2.037.09, 1990.

Delauney et al., "A Stable Bifunctional Antisense Transcript Inhibiting Gene Expression in Transgenic Plants," *Proc. Natl. Acad. Sci. USA*, 85:4300–4304, 1988.

Feig et al., "Somatic Activation of K–ras Gene in a Human Ovarian Carcinoma," *Science*, 223:698–701, 1984.

Finkel et al., "Activation of ras Genes in Human Tumors Does Not Affect Localization, Modification, or Nucleotide Binding Properties of p21," *Cell*, 37:151–158, 1984.

Griep and Heiner, "Antisense *Myc* Sequences Induce Differentiation of F9 Cells," *Proc natl. Acad. Sci. USA*, 85:6806–6810, 1988.

Gunning et al., "A Human β–Actin Expression Vector System Directs High–Level Accumulation of Antisense Transcripts," *Proc. Natl. Acad. Sci. USA*, 84:4831–4835, 1987.

Kasid et al., "Effect of Antisense *c–raf*–1 on Tumorigenicity and Radiation Sensitivity of a Human Squamous Carcinoma," *Science*, 243:1354–1356, 1989.

Khokha et al., "Antisense RNA–Induced Reduction in Murine TIMP Levels confers Oncogenicity on Swiss 3T3 Cells," *Science*, 243:947–950, 1989.

Kris et al., "Expression of K–Ras Oncogene in Tumor Cell Variants Exhibiting Different Metastatic Capabilities," *Int. J. Cancer*, 35:227–230, 1985.

Izant and Weintraub, "Inhibition of Thymidine Kinase Gene Expression by Anti–Sense RNA: A Molecular Approach to Genectic Analysis," *Cell*, 36:1007–1015, 1984.

Johnson et al., "Transfection of a Rat Cell Line with the v–Ki–ras Oncogene is Associated with Enhanced Susceptibility to Natural Killer Cell Lysis," *J. Exp. Med.*, 162:1732–1737, 1985.

McGrath et al., "Structure and Organization of the Human Ki–ras Protooncogene and a Related Processed Pseudogene," *Nature*, 304:501, 1983.

McGarth, "Tumor–Specific Antisense Oligonucleotides for Controlling Cancer," Abstract No. 114:55778n *Chemical Abstracts*, 114(7):68, 1991.

Mercola et al., "Antisense RNA: Enkaryotic Controls," *Gene*, 72:253–265, 1988.

Miller and Rosman, "Improved Retroviral Vectors for Gene Transfer and Expression," *BioTechniques*, 7(9):980–990, 1989.

Munroe, "Antisense RNA Inhibits Splicing of Pre–mRNA In Vitro," *The EMBO Journal*, 7(8):2523–2532, 1988.

Prochownik et al., "*c–myc* Antisense Transcripts Accelerate Differentiation and Inhibit G, Progression in Murine Erytholeukemia Cells," *Molecular and Cellular Biology*, 8(9):3683–3695, 1988.

Santos et al., "Malignant Activation of a K–ras Oncogene in Lung Carcinoma but Not in Normal Tissue of the Sam Patient," *Science*, 223:661–664, 1984.

Shimizu et al., "Structure of the Ki–ras Gene of the Human Lung Carcinoma Cell Line Calu–1," *Nature*, 304:497–500, 1983.

Stowers et al., "Activation of the K–ras Protooncogene in Lung Tumors from Rats and Mice Chronically Exposed to Tetranitromethane," *Cancer Research*, 47:3212–3219, 1987.

Taya et al., "A Novel Combination of *K–ras* and *myc* Amplification Accompanied by Point Mutational Activation of *K–ras* in a Human Lung Cancer," *The EMBO Journal*, 3(12):2943–2946, 1984.

Toftgard et al., "Proto–Oncogene Expression During Two–Stage Carcinogenesis in Mouse Skin," *Carcinogenesis*, 6(4):655–6657, 1985.

Vogelstein et al., "Genetic Alterations During Colorectal–Tumor Development," *The New England Journal of Medicine*, 319(9):525–532, 1988.

Wahran et al., *Tumour Biol.*, 6:41–56, 1985.

Winter and Perucho, "Oncogene Amplification During Tumorigenesis of Established Rat Fibroblasts Reversibly Transformed by Activated Human *ras* Oncogenes," *Molecular and Cellular Biology*, 6(7):2562–2570, 1986.

Wills and Menzel, "Adenovirus Vectors for Gene Therapy of Cancer," *Journal of Cellular Biochemistry*, p. 204, Abstract #S216, Mar.–Apr. 1993.

Zhang et al., "Generation and Identification of Recombinant Adenovirus by Liposome–Mediated Transfection and PCR™ Analysis," *BioTechniques*, 15(5):868–872, 1993.

Baker et al., "Chromosome 17 Deletions and p53 Gene Mutations in Colorectal Carinomas," *Science*, 244:217–221, Apr. 1989.

Baker et al., "Suppression of Human Colorectal Carcinoma Cell Growth by Wild–Type p53," *Science*, 249:912–915, Aug. 1990.

Baker et al., "p53 Gene Mutations Occur in Combination with 17p Allelic Deletions as Late Events in Colorectal Tumorigenesis," *Cancer Research*, 50:7717–7722, Dec. 1990.

Carter et al., "Adenovirus Containing a Deletion of the Early Region 2A Gene Allows Growth of Adeno–Associated Virus Decreased Efficiency," *Virology*, 191:473–476, 1992.

Diller et al., "p53 Functions as a Cell Cycle Control Protein in Osteosarcomns," *Molecular and Cellular Biology*, 10(11):5772–5781, Nov. 1990.

Eliyahu et al., "Meth A Fibrosarcoma Cells Express Two Transforming Mutant p53 Species," *Oncogene*, 3:313–321, 1988.

Eliyahu et al., "Wild–type p53 Can Inhibit Oncogene–Medicated Focus Formation," *Proc. Nat. Acad. Sci. USA*, 85:8763–8767, Nov. 1989.

Finlay et al., "The p53 Proto–Oncogene Can Act as a Suppressor of Transformation," *Cell*, 57:1083–1093, Jun. 1989.

Gebhardt et al., "A Tumor Suppressor Proto–Oncogene p53 Can Block Progression Through the Cell Cycle," Association of American Physicians, American Society for Clinical Investigation, American Federation for Clinical Research, Subspecialty Meetings, Sheraton Washington Hotel, Washington, DC, May 6, 1990, p. 447A, Abstract.

Graham and Prevec, "Manipulation of Adenovirus Vectos," *In: Methods in Molecular Biology: Gene Transfer and Expression Protocols*, E.J. Murray (ed.), The Humana Press, Inc., vol.7, Chapter 11, pp. 109–128, 1991.

Hinds et al., "The p53 Proto–Oncogene Can Suppress Transformation by Other Oncogenes, and Mutations on the Proto–Oncogene Can Activate the Gene for Transformation," *In: Common Mechanisms of Transformation by Small DNA Tumor Viruses*, Luis P. Villarreal (ed.), Chapter 7, pp. 83–101, 1989.

Hinds et al., "Mutation is Required to Activate the p53 Gene for Cooperation with the *ras* Oncogene and Transformation," *Journal of Virology*, 63(2):739–746, Feb. 1989.

Huang et al., "Suppression of the Neoplastic Phenotype by Replacement of the RB Gene in Human Cancer Cells," *Science*, 242:1563–1566, Dec. 1988.

Klessig et al., "Introduction, Stable Integration, and Controlled Expression of a Chimeric Adenovirus Gene Whose Product is Toxic to the Recipient Human Cell," *Molecular and Cellular Biology*, 4(7): 1354–1362, Jul. 1984.

Lamb and Crawford, "Characterization of the Human p53 Gene," *Molecular and Cellular Biology*, 6(5):1379–1385, May 1986.

Levine et al., "The p53 Growth Suppressing Gene Can Inhibit Transformation by Other Oncogenes," *The Journal of Cell Biology*, The American Society for Cell Biology, Twenty–ninth Annual Meeting, Houston, Texas, Nov. 5–9, 1989, Abstract 502.

Malkin et al., "Mutant p53 Confers Tumorigenicity to a Cell Line Lacking p53: Evidence for a Second p53 Function in Tumor Formation," *Blood*, 76(10, Suppl. 1):238a, Abstract 944, 1990.

Mercer et al., "Negative Growth Regulation in a Glioblastoma Tumor Cell Line that Conditionally Expresses Human Wild–Type p53," *Proc. Natl. Acad. Sci. USA*, 87:6166–6170, Aug. 1990.

Nigro et al., "Mutations in the *p53* Gene Occur in Diverse Human Tumor Types," *Nature*, 342:705–708, Dec. 1989.

Sager, "Tumor Suppressor Genes: The Puzzle and the Promise," *Science*, 246:1406–1412, Dec. 1989.

Vogelstein et al., "Genetic Alterations Accumulate During Colorectal Tumorigenesis," Feb. 3–Mar. 11, 1990, *Journal of Cellular Biochemistry, Negative Controls on Cell Growth*, Abstracts, p. 251, Supplement 14C, 1990, Abstract 1004.

Pfarr et al., "Differential Effects of Polyadenylation Regions on Gene Expression in Mammalian Cells," *DNA*, 5(2):115–122, 1986.

Eliyahu et al., "p53—A Potential Suppressor Gene?" *Journal of Cellular Biochemistry*, UCLA Symposia on Molecular & Cellular Biology, Abstracts, 19th Annual Meeting, Supplement 14C:264, Abstract No. I 030, Feb. 3–Mar. 11, 1990.

Hinds, "Biological Consequences of Mutation of the p53 Proto–Oncogene," *UMI Dissertation Services*, Oct. 1989.

Lee et al., "Molecular Basis of Tumor Suppression by the Human Retinoblastoma Gene," *Journal of Cellular Biochemistry*, UCLA Symposia on Molecular & Cellular Biology, Abstracts, 19th Annual Meeting, Supplement 14C, Abstract No. I 001, Feb. 3–Mar. 11, 1990.

Levine et al., "The p53 Growth Suppressor Gene," *Journal of Cellular Biochemistry*, UCLA Symposia on Molecular & Cellular Biology, Abstracts, 19th Annual Meeting, Supplement 14C:264, Abstract No. I 029, Feb. 3–Mar. 11, 1990.

Mercer et al., "Antiproliferative Effects of Wild Type Human P53," *Journal of Cellular Biochemistry*, UCLA Symposia on Molecular & Cellular Biology, Abstracts, 19th Annual Meeting, Supplement I4C:264, Abstract No. I 224, Feb. 3–Mar. 11, 1990.

Minna et al., "The Molecular Pathogenesis of Lung Cancer Involves the Accumulation of a Large Number of Mutations in Dominant Oncogenes and Multiple Tumor Suppressor Genes (Recessive Oncogenes)," *Journal of Cellular Biochemistry*, UCLA Symposia on Molecular & Cellular Biology, Abstracts, 19th Annual Meeting, Supplement 14C:264, Abstract No. I 003, Feb. 3–Mar. 11, 1990.

Boehringer Mannheim Brochure, "Transfection–Reagent (DOTAP)", pp. 214–217, 1991.

Pasleau et al., "Growth hormone gene expression in eukaryotic cells directed by the Rous sarcoma virus long termainal repeat or cytomegalovirus immediate–early promoter," *Gene*, 38:227–232, 1985.

Quantin et al., "Adnovirus as an expression vector in muscle cells in vivo," *PNAC USA*, 89:2581–2584, 1992.

\* cited by examiner

RECOMBINANT P53 ADENOVIRUS METHODS AND COMPOSITIONS

This application is a continuation of 08/145,826 filed Oct. 29, 1993 now U.S. Pat. No. 6,410,010 which is a continuation-in-part of U.S. patent application Ser. No. 07/960,513, filed Oct. 13, 1992 now U.S. Pat. No. 6,017,524, the entire text of which is herein incorporated by reference without disclaimer. The government owns rights in the present invention pursuant to NIH grants RO1 CA 45187 and CA 16672.

BACKGROUND OF THE INVENTION

1. Field of the Invention

The present invention relates generally to the area of recombinant technology. In some aspects, it concerns simplified and efficient methods of generating recombinant adenovirus. In other aspects, novel compositions and methods involving p53 adenovirus constructs are provided, including methods for restoring normal p53 functions and growth suppression to cells with abnormal p53.

2. Description of Related Art

Current treatment methods for cancer, including radiation therapy, surgery, and chemotherapy, are known to have limited effectiveness. Lung cancer alone kills more than 140,000 people annually in the United States. Recently, age-adjusted mortality from lung cancer has surpassed that from breast cancer in women. Although implementation of smoking-reduction programs has decreased the prevalence of smoking, lung cancer mortality rates will remain high well into the 21st century. The rational development of new therapies for lung cancer will depend on an understanding of the biology of lung cancer at the molecular level.

It is now well established that a variety of cancers are caused, at least in part, by genetic abnormalities that result in either the over expression of one or more genes, or the expression of an abnormal or mutant gene or genes. For example, in many cases, the expression of oncogenes is known to result in the development of cancer. "Oncogenes" are genetically altered genes whose mutated expression product somehow disrupts normal cellular function or control (Spandidos et al., 1989).

Most oncogenes studied to date have been found to be "activated" as the result of a mutation, often a point mutation, in the coding region of a normal cellular gene, i.e., a "proto-oncogene", that results in amino acid substitutions in the expressed protein product. This altered expression product exhibits an abnormal biological function that takes part in the neoplastic process (Travali et al., 1990). The underlying mutations can arise by various means, such as by chemical mutagenesis or ionizing radiation. A number of oncogenes and oncogene families, including ras, myc, neu, raf, erb, src, fms, jun and abl, have now been identified and characterized to varying degrees (Travali et al., 1990; Bishop, 1987).

During normal cell growth, it is thought that growth-promoting proto-oncogenes are counterbalanced by growth-constraining rumor suppressor genes. Several factors may contribute to an imbalance in these two forces, leading to the neoplastic state. One such factor is mutations in tumor suppressor genes (Weinberg, 1991).

An important tumor suppressor gene is the gene encoding the cellular protein, p53, which is a 53 kD nuclear phosphoprotein that controls cell proliferation. Mutations to the p53 gene and allele loss on chromosome 17p, where this gene is located, are among the most frequent alterations identified in human malignancies. The p53 protein is highly conserved through evolution and is expressed in most normal tissues. Wild-type p53 has been shown to be involved in control of the cell cycle (Mercer, 1992), transcriptional regulation (Fields et al., 1990, and Mietz et al., 1992), DNA replication (Wilcock and Lane, 1991, and Bargonetti et al., 1991), and induction of apoptosis (Yonish-Rouach et al., 1991, and, Shaw et al., 1992).

Various mutant p53 alleles are known in which a single base substitution results in the synthesis of proteins that have quite different growth regulatory properties and, ultimately, lead to malignancies (Hollstein et al., 1991). In fact, the p53 gene has been found to be the most frequently mutated gene in common human cancers (Hollstein et al., 1991: Weinberg. 1991), and is particularly associated with those cancers linked to cigarette smoke (Hollstein et al., 1991; Zakut-Houri et al., 1985). The overexpression of p53 in breast tumors has also been documented (Casey et al., 1991).

One of the most challenging aspects of gene therapy for cancer relates to utilization of tumor suppressor genes, such as p53. It has been reported that transfection of wild-type p53 into certain types of breast and lung cancer cells can restore growth suppression control in cell lines (Casey et al., 1991; Takahasi et al., 1992). Although DNA transfection is not a viable means for introducing DNA into patients' cells, these results serve to demonstrate that supplying wild type p53 to cancer cells having a mutated p53 gene may be an effective treatment method if an improved means for delivering the p53 gene could be developed.

Gene delivery systems applicable to gene therapy for tumor suppression are currently being investigated and developed. Virus-based gene transfer vehicles are of particular interest because of the efficiency of viruses in infecting actual living cells, a process in which the viral genetic material itself is transferred. Some progress has been made in this regard as, for example, in the generation of retroviral vectors engineered to deliver a variety of genes. However, major problems are associated with using retroviral vectors for gene therapy since their infectivity depends on the availability of retroviral receptors on the target cells, they are difficult to concentrate and purify, and they only integrate efficiently into replicating cells.

Adenovirus vector systems have recently been proposed for use in certain gene transfer protocols, however, the current methods for preparing recombinant adenovirus have several drawbacks. These methods rely on calcium phosphate-mediated transfection of expression vectors and adenoviral plasmids into host cells and subsequent plaque assays on the transfected cells. These types of transfection steps and assays are inefficient and typically result in low levels of viral propagation.

There remains, therefore, a clear need for the development of new methods for introducing tumor suppressor genes, such as p53, into cells as a means for restoring growth suppression. Methods for producing recombinant adenovirus which avoid calcium-phosphate mediated transfection and agarose overlay for plaque assays would also be advantageous.

SUMMARY OF THE INVENTION

The present invention addresses the foregoing and other problems by providing efficient methods for producing recombinant adenovirus, such as p53 adenovirus, and effective means by which to restore p53 functions to cells with aberrant p53. Recombinant adenovirus vectors and virions are disclosed, as are methods of using such compositions to promote wild type p53 expression in cells with aberrant p53 functions, such as cancer cells. Also disclosed is a simplified protocol for propagating recombinant adenovirus using liposome-mediated DNA transfection followed by observation of cytopathic effect (CPE) and, preferably, polymerase chain reaction (PCR) analysis.

Furthermore, utilizing this new method for generating and propagating recombinant adenoviruses, it is envisaged that other genes may be incorporated into the virion genome. These genes could include tumor suppressor genes such as the retinoblastoma (rb) gene, antisense oncogenes, i.e. anti-c-myc and anti-k-ras, and other growth control related genes for cancer gene therapy.

Using the present invention the inventors have demonstrated a remarkable effect in controlling metastatic growth. The Ad5CMV-p53 recombinant adenovirus was shown to markedly reduce the growth rate of transformed cells. The virus inhibited tumorigenicity of virus-infected H358 cells. Furthermore it prevented orthotopic lung cancer growth when the virus was instilled intratracheally following the intratracheal inoculation of the H226Br cells. The inhibition of tumorigenicity also suggests that even transient expression of a high-level of the p53 protein may be enough to induce a tumoricidal effect.

In one specific embodiment, this invention concerns vector constructs for introducing wild type p53 genes into target cells, such as target cells suspected of having mutant or aberrant p53 genes, including malignant cell types. These embodiments involve the preparation of a gene expression or transcription unit wherein the p53 gene is placed under the control of a promoter and the unit is incorporated into an adenoviral vector within a recombinant adenovirus. The invention as a whole is surprising and advantageous for several reasons. Firstly, it was previously thought that p53 virus could not be generated into a packaging cell, such as those used to prepare adenovirus, as it would be toxic; secondly, E1B of adenovirus binds to p53 and thus interferes with its function; thirdly, once generated, the p53 adenovirus was found to be unexpectedly effective at inhibiting the growth of various cancer cells; and finally the tumorigenicity of the lung cancer cells was inhibited through the treatment by Ad5CMV-p53 but not a control virus indicating that the novel p53 protein delivery and preparation has astonishing therapeutic efficacy.

The invention therefore concerns adenovirus vector constructs that involve using Adenovirus to carry tumor suppressor genes such as p53, anti-sense oncogenes and other related genes for human cancer therapy. In one embodiment recombinant Adenovirus virions or particles incorporating such vectors, and pharmacological formulations thereof, which comprise a recombinant insert including an expression region encoding wild type p53, by which vectors are capable of expressing p53 in human metastatic cells are encompassed. The p53 expression region in the vector may comprise a genomic sequence, but for simplicity, it is contemplated that one will generally prefer to employ a p53 cDNA sequence as these are readily available in the art and more easily manipulated. The recombinant insert of the vector will also generally comprise a promoter region and a polyadenylation signal, such as an SV40 or protamine gene polyadenylation signal.

In preferred embodiments, it is contemplated that one will desire to position the p53 expression region under the control of a strong constitutive promoter such as a CMV promoter, viral LTR, RSV, or SV40 promoter, or a promoter associated with genes that are expressed at high levels in mammalian cells such as elongation factor-1 or actin promoters. Currently, the most preferred promoter is the cytomegalovirus (CMV) IE promoter.

The p53 gene or cDNA may be introduced into recombinant adenovirus in accordance with the invention simply by inserting or adding the p53 coding sequence into a viral genome which lacks E1B. However, the preferred adenoviruses will be replication defective viruses in which a viral gene essential for replication and/or packaging has been deleted from the adenoviral vector construct, allowing the p53 expression region to be introduced in its place. Any gene in addition to E1B, whether essential (e.g., E1A, E2 and E4) or non-essential (e.g., E3) for replication, may be deleted and replaced with p53.

Particularly preferred are those vectors and virions in which the E1A and E1B regions of the adenovirus vector have been deleted and the p53 expression region introduced in their place, as exemplified by the genome structure of FIG. 1.

Techniques for preparing replication defective adenoviruses are well known in the art, as exemplified by Ghosh-Choudhury and Graham (1987); McGrory et al. (1988); and Gluzman et al. (1982), each incorporated herein by reference. It is also well known that various cell lines may be used to propagate recombinant adenoviruses, so long as they complement any replication defect which may be present. A preferred cell line is the human 293 cell line, but any other cell line that is permissive for replication, i.e., in the preferred case, which expresses E1A and E1B may be employed. Further, the cells can be propagated either on plastic dishes or in suspension culture, in order to obtain virus stocks thereof.

The invention is not limited to E1-lacking virus and E1-expressing cells alone. Indeed, other complementary combinations of viruses and host cells may be employed in connection with the present invention, so long as the p53 vector does not have E1B. Virus lacking functional E2 and E2-expressing cells may be used, as may virus lacking functional E4 and E4-expressing cells, and the like. Where a gene which is not essential for replication is deleted and replaced, such as, for example, the E3 gene, this defect will not need to be specifically complemented by the host cell.

Other than the requirement that the adenovirus vectors and virions not have E1B, their nature is not believed to be crucial to the successful practice of the invention. The adenovirus may be of any of the 42 different known serotypes or subgroups A–F. Adenovirus type 5 of subgroup C is the preferred starting material in order to obtain the conditional replication-defective adenovirus vector for use in the method of the present invention. This is because Adenovirus type 5 is a human adenovirus about which there is significant amount of biochemical and genetic information known, and which has historically been used for most constructions employing adenovirus as a vector.

Further related aspects of the invention concern novel p53 DNA segments, or expression vectors, and recombinant host cells which incorporate an adenoviral p53 vector prepared in accordance herewith. The DNA segments of the invention will generally comprise, in the 5'–3' direction of transcription, a cytomegalovirus IE promoter, a structural gene for the wild-type human p53, and an SV40 early polyadenylation signal. The recombinant adenovirus-containing host cell will generally be a eukaryotic or mammalian host cell, such as a 293 cell, or may be a cell with a defect in a p53 gene which has been infected with the adenovirus of the invention.

Other embodiments concern pharmaceutical compositions comprising a recombinant adenovirus which encodes wild type p53, dispersed in a pharmacologically acceptable solution or buffer. Preferred pharmacologically acceptable solutions include neutral saline solutions buffered with phosphate, lactate, Tris, and the like. Of course, one will desire to purify the adenovirus sufficiently to render it essentially free of undesirable contaminants, such as defective interfering adenovirus particles or endotoxins and other pyrogens such that it will not cause any untoward reactions in the animal or individual receiving the vector construct. A preferred means of purifying the vector involves the use of buoyant density gradients, such as cesium chloride gradient centrifugation.

In still further embodiments, the invention relates to a method for providing p53 functions, or restoring wild-type p53 protein functions, to a cell deficient in wild-type p53. To achieve this, one would contact the cell bearing the p53 mutation with an amount of recombinant adenovirus of the invention effective to express wild-type p53 in the cell. This may be achieved by administering a physiologically effective amount of a pharmaceutical composition comprising the adenovirus to an animal or human subject which harbors cells with defective p53, such as, e.g., cancer cells. Therefore, the present invention also encompasses effective methods for treating human malignancies such as breast and lung cancer.

In another embodiment of the invention the p53 expressing adenovirus is used to prevent malignant and even metastatic growth. In one embodiment the recombinant p53 expressing adenovirus is used to inhibit the uncontrolled growth of cells that have mutations of the p53 gene. In a more preferred embodiment the p53 expressing adenovirus inhibits the tumorigenicity and growth of H358 cells, but any other cell that is an indicator of p53 function may be used.

In a further embodiment the p53 expressing virus is used to prevent orthotopic lung tumor growth when the virus is instilled intratracheally. The Ad5CMV-p53 virus yielded encouraging results in the nude mouse tests. The virus inhibited tumorigenicity of virus-infected H358 cells, a cell that normally produces a significant tumor mass. The virus also prevented orthotopic lung cancer growth when the virus was instilled intratracheally following the intratracheal inoculation of H226Br cells confirming the in vitro effects of Ad5CMV-p53 on the lung cancer cells. The tumorigenicity of the lung cancer cells was inhibited through the treatment by Ad5CMV-p53 but not by the control virus Ad5/RSV/GL2. indicating that the p53 protein has therapeutic efficacy. It will be understood by those skilled in the art that other methods of viral delivery are encompassed by the invention.

While aspects of the invention are exemplified through the use of p53 constructs in connection with restoring normal cell function and for use in cancer treatment, it is proposed that the invention is generally applicable to any situation where one desires to achieve high level expression of a tumor suppressor protein in a target or host cell through the use of recombinant adenovirus. For example, in the context of cancer treatment modalities, a particular example in addition to p53 replacement that is contemplated by the inventors is the introduction of the retinoblastoma gene (rb), anti-sense oncogenes (c-myc or c-ras), and other related genes for human cancer therapy.

It should be pointed out that because the adenovirus vector employed is replication defective, it will not be capable of replicating in the cells, such as cancer cells, that are ultimately infected. Thus, where continued treatment in certain individuals is required, such as at the beginning of therapy, it may be necessary to reintroduce the virus after a certain period, for example, 6 months or a year.

The adenoviral vectors of the present invention will also have utility in embodiments other than those connected directly with gene therapy. Alternative uses include, for example, in vitro analyses and mutagenesis studies of various p53 genes, and the recombinant production of proteins for use, for example, in antibody generation or other embodiments. In embodiments other than those connected with human therapy, including all those concerned with further defining the molecular activity of p53, other related viruses may even be employed to deliver p53 to a cell. Those belonging to the herpes family, e.g., herpes simplex virus (HSV), Epstein-Barr Virus (EBV), cytomegalovirus (CMV) and pseudorabies virus (PRV) would be suitable.

A different aspect of the present invention concerns simplified procedures for producing any type of recombinant adenovirus which avoid using the inefficient calcium phosphate transfection and tedious plaque assays. To produce recombinant adenovirus in accordance with the present invention, one would generally introduce an adenovirus plasmid and an expression vector into a suitable host cell by liposome-mediated transfection, and then analyze the cultured host cell for the presence of a cytopathic effect (CPE), which is indicative of homologous recombination and virus production. It is the increase in transfection efficiency of the first step which renders the second and advantageous CPE step possible.

A preferred composition for use in the liposome-mediated transfection is DOTAP (N-[1-(2,3-dideoyloxy)propyl]-N,N, N-trimethyl-ammoniummethysulfate) which is commercially available. CPE is a directly observable phenomenon, which may be assessed using phase contrast microscopy. CPE describes the morphologic features of Adenovirus cytotoxicity that begin with the shrinking of the lytically infected cell and conclude with the formation of a lytic plaque. A particular advantage of this method is that viral propagation is readily determined after a 10 to 14 day incubation. This is a significant improvement over the calcium phosphate-mediated transfection and subsequent plaque assays require at least 14 and usually up to a minimum of 21 days, and frequently up to several weeks before the results can be assessed.

In certain embodiments, the method of the invention may be used in connection with adenovirus plasmids which are replication-defective, along with a host cell which complements the defect, as exemplified by E1-lacking plasmids and 293 cells. Adenovirus plasmids which lack functional E1A and E1B and which incorporate a p53 expression region are used herein in working examples of the invention, but any expression region may be incorporated into a recombinant adenovirus in this manner. The precise methodological aspects may be varied as desired; however, it is contemplated that the use of MEM media will be preferred in certain cases.

These new methods may be combined with PCR analysis to confirm the presence of the correctly recombined virus. PCR is well known to those in the art, as disclosed in U.S. Pat. No. 4,683,195, incorporated herein by reference. To use PCR in connection with the invention, one would obtain DNA from the supernatant of cells exhibiting a cytopathic effect and analyze the DNA by PCR using two pairs of primers, one expression vector-specific and the other adenoviral genome-specific DNA primers. Vector- or insert-specific DNA is, by definition, a gene segment which is part of the DNA encoding the polypeptide or RNA one ultimately desires to be expressed, as illustrated by p53 DNA expression as mRNA and protein production. Adenovirus genome specific DNA may be any part of the genome that is expressed during the stage of propagation being monitored.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 3A, 3B, 3C and 3D are a series of phase contrast images (×400) of 293 cells. FIGS. 3A, 3B, 3C and 3D are four panels of a single page figure. FIG. 2A, before transfection; FIG. 3B, negative control on day 12 posttransfection; FIG. 3C, onset of CPE on day 12 posttransfection; FIG. 3D, completion of CPE on day 14 post-transfection FIGS. 4A, 4B, 4C, and 4D, immunohistology of cells infected with recombinant adenoviruses. FIGS. 4A, 4B, 4C and 4D are four panels of a single page figure. Infectivity of Ad5CMV-p53 in H358 cells. H358 cells were infected with Ad5CMV-p53 or Ad5/RSV/GL2 at 50 PFU/cell for 24 h. Medium alone was used as a mock infection. The infected cells were analyzed by immunostainings. FIG. 4A is a mock infection probed with anti-p53 antibody. FIG. 4B are cells infected with the Ad5/RSV/G2 control and probed with anti-p53 antibody. FIG. 4C are Ad5CMV-p53 infected cells probed with an unrelated antibody (MOPC-21). FIG. 4D are cells Ad5CMV-p53 infection probed with anti-p53 antibody. The anti-p53 antibody used was Pab 1801, and the avidin-biotin method was used for staining.

FIGS. 9A, 9B, 9C, and 9D are four panels of a single figure. The mice were sacrificed at the end of the 6-week posttreatment period. The lung and mediastinum tissues were dissected for evaluation of tumor formation. FIG. 9A is a sample of mediastinal block from a normal nude mice. FIG. 9B is the mediastinal block sample from the vehicle (PBS)-treated mice; FIG. 9C is the mediastinal block sample from the Ad5CMV-p53-treated mice; FIG. 9D is the mediastinal block sample from the Ad5/RSV/GL2-treated mice. Arrows indicate the tumor masses.

DETAILED DESCRIPTION OF THE PREFERRED EMBODIMENTS

Figure 1:
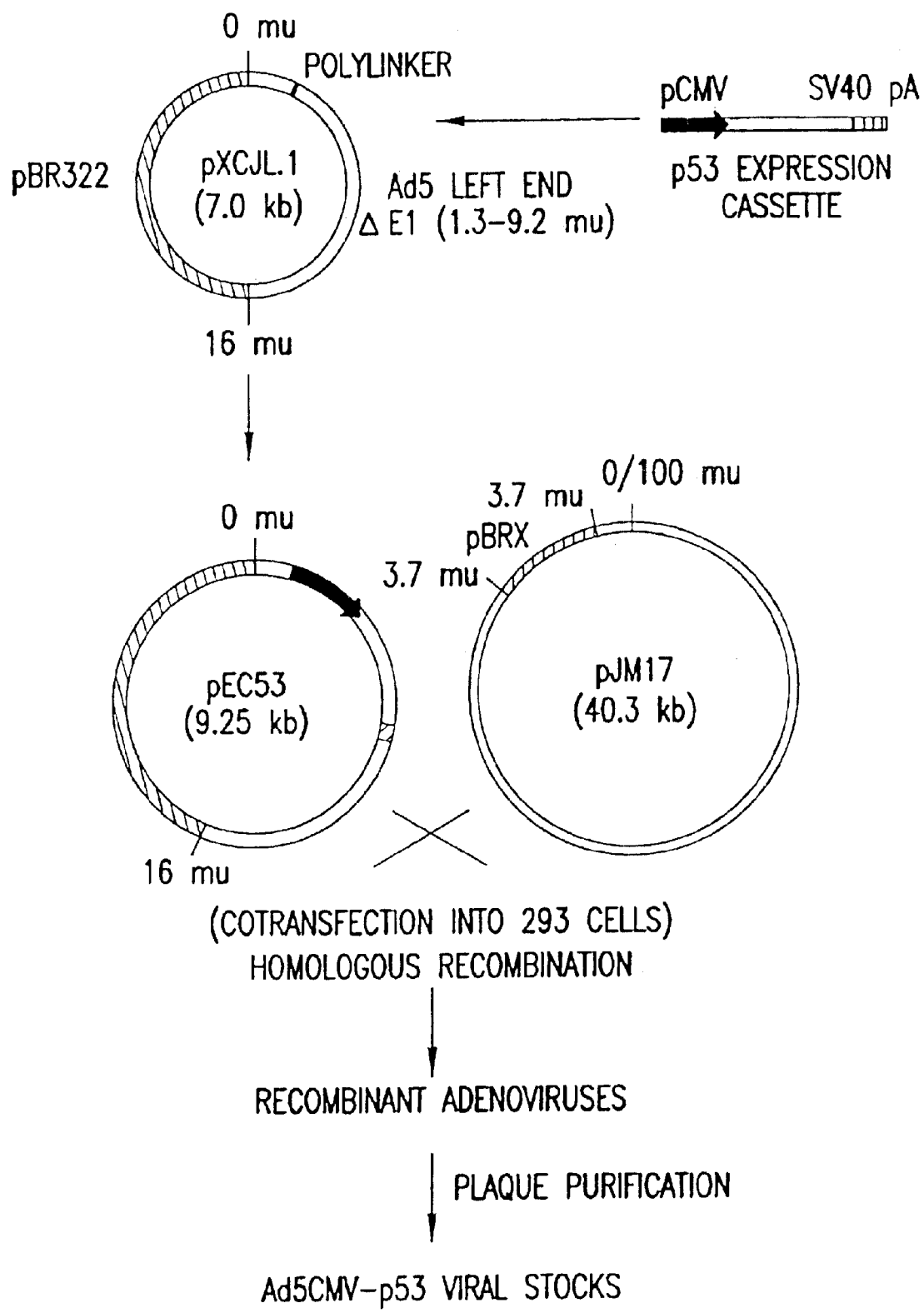
FIG. 1. Scheme for generation of recombinant p53 adenovirus. The p53 expression cassette was inserted between the Xba I and Cla I sites of pXCJL.1. The p53 expression vector (pEC53) and the recombinant plasmid pJM17 were cotransfected into 293 cells. The transfected cells were maintained in medium until the onset of the cytopathic effect. Identification of newly generated p53 recombinant adenoviruses (Ad5CMV-p53) by PCR analysis of the DNA using DNA templates prepared from the CPE supernatants treated with Proteinase K and phenol extraction.

A. Molecular Events in Lung Cancer Development

Studies carried out by the present inventors has identified critical molecular events leading to the development and progression of cancer. This enabled the inventors to develop new methods for restoring certain normal protein functions so that the malignant phenotype can be suppressed in vivo.

The most common lung cancer histologies (80%) are grouped under the term non-small-cell lung cancer (NSCLC) and include squamous, adenocarcinoma, and large-cell undifferentiated. Many of the current data on the molecular biology of lung cancer come from the study of the more uncommon small-cell lung cancer (SCLC). SCLC can be distinguished from NSCLC by the neuroendocrine features of the cells; SCLC is very responsive to chemotherapy but recurs rapidly after treatment. NSCLC also may serve as a model for other carcinogen-induced epithelial cancers. The approaches and observations developed in this study may be applicable to other types of epithelial cancers.

Abundant evidence has accumulated that the process of malignant transformation is mediated by a genetic paradigm. The major lesions detected in cancer cells occur in dominant oncogenes and tumor suppressor genes. Dominant oncogenes have alterations in a class of genes called proto-oncogenes, which participate in critical normal cell functions, including signal transduction and transcription. Primary modifications in the dominant oncogenes that confer the ability to transform include point mutations, translocations, rearrangements, and amplification. Tumor suppressor genes appear to require homozygous loss of function, by mutation, deletion, or a combination of these for transformation to occur. Some tumor suppressor genes appear to play a role in the governance of proliferation by regulation of transcription. Modification of the expression of dominant and tumor suppressor oncogenes is likely to influence certain characteristics of cells that contribute to the malignant phenotype.

Despite increasing knowledge of the mechanisms involved in oncogene-mediated transformation, little progress has occurred in developing therapeutic strategies that specifically target oncogenes and their products. Initially, research in this area was focused on dominant oncogenes, as these were the first to be characterized. DNA-mediated gene transfer studies showed acquisition of the malignant phenotype by normal cells following the transfer of DNA from malignant human tumors.

B. p53 and p53 Mutations in Cancer

P53 is currently recognized as a tumor suppressor gene (Montenarh, 1992). High levels have been found in many cells transformed by chemical carcinogenesis, ultraviolet radiation, and several viruses, including SV40. The p53 gene is a frequent target of mutational inactivation in a wide variety of human tumors and is already documented to be the most frequently-mutated gene in common human cancers (Mercer, 1992). It is mutated in over 50% of human NSCLC (Hollestein et al., 1991) and in a wide spectrum of other tumors.

The p53 gene encodes a 375-amino-acid phosphoprotein that can form complexes with host proteins such as large-T antigen and E1B. The protein is found in normal tissues and cells, but at concentrations which are minute by comparison with transformed cells or tumor tissue. Interestingly, wild-type p53 appears to be important in regulating cell growth and division. Overexpression of wild-type p53 has been shown in some cases to be anti-proliferative in human tumor cell lines. Thus p53 can act as a negative regulator of cell growth (Weinberg, 1991) and may directly suppress uncontrolled cell growth or indirectly activate genes that suppress this growth. Thus, absence or inactivation of wild type p53 may contribute to transformation. However, some studies indicate that the presence of mutant p53 may be necessary for full expression of the transforming potential of the gene.

Although wild-type p53 is recognized as a centrally important growth regulator in many cell types, its genetic and biochemical traits appear to have a role as well. Missense mutations are common for the p53 gene and are essential for the transforming ability of the oncogene. A single genetic change prompted by point mutations can create carcinogenic p53. Unlike other oncogenes, however, p53 point mutations are known to occur in at least 30 distinct codons, often creating dominant alleles that produce shifts in cell phenotype without a reduction to homozygosity. Additionally, many of these dominant negative alleles appear to be tolerated in the organism and passed on in the germ line. Various mutant alleles appear to range from minimally dysfunctional to strongly penetrant, dominant negative alleles (Weinberg. 1991).

Casey and colleagues have reported that transfection of DNA encoding wild-type p53 into two human breast cancer cell lines restores growth suppression control in such cells (Casey et al., 1991). A similar effect has also been demonstrated on transfection of wild-type, but not mutant, p53 into human lung cancer cell lines (Takahasi et al., 1992). The p53 appears dominant over the mutant gene and will select against proliferation when transfected into cells with the mutant gene. Normal expression of the transfected p53 does not affect the growth of cells with endogenous p53. Thus, such constructs might be taken up by normal cells without adverse effects.

It is thus possible that the treatment of p53-associated cancers with wild type p53 may reduce the number of malignant cells. However, studies such as those described above are far from achieving such a goal, not least because DNA transfection cannot be employed to introduce DNA into cancer cells within a patients' body.

C. Gene Therapy Techniques

There have been several experimental approaches to gene therapy proposed to date, but each suffer from their particular drawbacks (Mulligan, 1993). As mentioned above, basic transfection methods exist in which DNA containing the gene of interest is introduced into cells non-biologically, for example, by permeabilizing the cell membrane physically or chemically. Naturally, this approach is limited to cells that can be temporarily removed from the body and can tolerate the cytotoxicity of the treatment, i.e. lymphocytes. Liposomes or protein conjugates formed with certain lipids and amphophilic peptides can be used for transfection, but the efficiency of gene integration is still very low, on the order of one integration event per 1,000 to 100,000 cells, and expression of transfected genes is often limited to days in proliferating cells or weeks in non proliferating cells. DNA transfection is clearly, therefore, not a suitable method for cancer treatment.

A second approach capitalizes on the natural ability of viruses to enter cells, bringing their own genetic material with them. Retroviruses have promise as gene delivery vectors due to their ability to integrate their genes into the host genome, transferring a large amount of foreign genetic material, infecting a broad spectrum of species and cell types and of being packaged in special cell-lines. However, three major problems hamper the practical use of retrovirus vectors. First, retroviral infectivity depends on the availability of the viral receptors on the target surface. Second, retroviruses only integrate efficiently into replicating cells. And finally, retroviruses are difficult to concentrate and purify.

D. Adenovirus Constructs for use in Gene Therapy

Human adenoviruses are double-stranded DNA tumor viruses with genome sizes of approximate 36 kb (Tooza, 1981). As a model system for eukaryotic gene expression, adenoviruses have been widely studied and well characterized, which makes them an attractive system for development of adenovirus as a gene transfer system. This group of viruses is easy to grow and manipulate, and they exhibit a broad host range in vitro and in vivo. In lytically infected cells, adenoviruses are capable of shutting off host protein synthesis, directing cellular machineries to synthesize large quantities of viral proteins, and producing copious amounts of virus.

The E1 region of the genome includes E1A and E1B which encode proteins responsible for transcription regulation of the viral genome, as well as a few cellular genes. E2 expression, including E2A and E2B, allows synthesis of viral replicative functions, e.g. DNA-binding protein, DNA polymerase, and a terminal protein that primes replication. E3 gene products prevent cytolysis by cytotoxic T cells and tumor necrosis factor and appear to be important for viral propagation. Functions associated with the E4 proteins include DNA replication, late gene expression, and host cell shutoff. The late gene products include most of the virion capsid proteins, and these are expressed only after most of the processing of a single primary transcript from the major late promoter has occurred. The major late promoter (MLP) exhibits high efficiency during the late phase of the infection (Stratford-Perricaudet and Perricaudet, 1991a).

As only a small portion of the viral genome appears to be required in cis (Tooza, 1981), adenovirus-derived vectors offer excellent potential for the substitution of large DNA fragments when used in connection with cell lines such as 293 cells. Ad5-transformed human embryonic kidney cell line (Graham, et al., 1977) have been developed to provide the essential viral proteins in trans. The inventors thus reasoned that the characteristics of adenoviruses rendered them good candidates for use in targeting cancer cells in vivo (Grunhaus & Horwitz, 1992).

Particular advantages of an adenovirus system for delivering foreign proteins to a cell include (i) the ability to substitute relatively large pieces of viral DNA by foreign DNA; (ii) the structural stability of recombinant adenoviruses; (iii) the safety of adenoviral administration to humans; and (iv) lack of any known association of adenoviral infection with cancer or malignancies; (v) the ability to obtain high titers of the recombinant virus; and (vi) the high infectivity of Adenovirus.

Further advantages of adenovirus vectors over retroviruses include the higher levels of gene expression. Additionally, adenovirus replication is independent of gene replication, unlike retroviral sequences. Because adenovirus transforming genes in the E1 region can be readily deleted and still provide efficient expression vectors, oncogenic risk from adenovirus vectors is thought to be negligible (Grunhaus & Horwitz, 1992).

In general, adenovirus gene transfer systems are based upon recombinant, engineered adenovirus which is rendered replication-incompetent by deletion of a portion of its genome, such as E1, and yet still retains its competency for infection. Relatively large foreign proteins can be expressed when additional deletions are made in the adenovirus genome. For example, adenoviruses deleted in both E1 and E3 regions are capable of carrying up to 10 Kb of foreign DNA and can be grown to high titers in 293 cells (Stratford-Perricaudet and Perricaudet, 1991a). Surprisingly persistent expression of transgenes following adenoviral infection has also been reported.

Adenovirus-mediated gene transfer has recently been investigated as a means of mediating gene transfer into eukaryotic cells and into whole animals. For example, in treating mice with the rare recessive genetic disorder ornithine transcarbamylase (OTC) deficiency, it was found that adenoviral constructs could be employed to supply the normal OTC enzyme. Unfortunately, the expression of normal levels of OTC was only achieved in 4 out of 17 instances (Stratford-Perricaudet et al., 1991b). Therefore, the defect was only partially corrected in most of the mice and led to no physiological or phenotypic change. These type of results therefore offer little encouragement for the use of adenoviral vectors in cancer therapy.

Attempts to use adenovirus to transfer the gene for cystic fibrosis transmembrane conductance regulator (CFTR) into the pulmonary epithelium of cotton rats have also been partially successful, although it has not been possible to assess the biological activity of the transferred gene in the epithelium of the animals (Rosenfeld et al., 1992). Again, these studies demonstrated gene transfer and expression of the CFTR protein in lung airway cells but showed no physiologic effect. In the 1991 Science article, Rosenfeld et al. showed lung expression of $\alpha$1-antitrypsin protein but again showed no physiologic effect. In fact, they estimated that the levels of expression that they observed were only about 2% of the level required for protection of the lung in humans, i.e., far below that necessary for a physiologic effect.

The gene for human $\alpha_1$-antitrypsin has been introduced into the liver of normal rats by intraportal injection, where it was expressed and resulted in the secretion of the introduced human protein into the plasma of these rats (Jaffe et al., 1992). However, and disappointingly, the levels that were obtained were not high enough to be of therapeutic value.

These type of results do not demonstrate that adenovirus is able to direct the expression of sufficient protein in recombinant cells to achieve a physiologically relevant effect, and they do not, therefore, suggest a usefulness of the adenovirus system for use in connection with cancer therapy. Furthermore, prior to the present invention, it was thought that p53 could not be incorporated into a packaging cell, such as those used to prepare adenovirus, as it would be toxic. As E1B of adenovirus binds to p53, this was thought to be a further reason why adenovirus and p53 technology could not be combined.

E. p53-Adenovirus Constructs and Tumor Suppression

The present invention provides cancer gene therapy with a new and more effective tumor suppressor vector. This recombinant virus exploits the advantages of adenoviral vectors, such as high titer, broad target range, efficient transduction, and non-integration in target cells. In one embodiment of the invention, a replication-defective, helper-independent adenovirus is created that expresses wild type p53 (Ad5CMV-p53) under the control of the human cytomegalovirus promoter.

Control functions on expression vectors are often provided from viruses when expression is desired in mammalian cells. For example, commonly used promoters are derived from polyoma, adenovirus 2 and simian virus 40 (SV40). The early and late promoters of SV40 virus are particularly useful because both are obtained easily from the virus as a fragment which also contains the SV40 viral origin of replication. Smaller or larger SV40 fragments may also be used provided there is included the approximately 250 bp sequence extending from the HindIII site toward the BglI site located in the viral origin of replication. Further, it is also possible, and often desirable, to utilize promoter or control sequences normally associated with the included gene sequence, provided such control sequences are compatible with the host cell systems.

An origin of replication may be provided by construction of the vector to include an exogenous origin, such as may be derived from SV40 or other viral (e.g., polyoma, adeno, VSV, BPV) source, or may be provided by the host cell chromosomal replication mechanism. If the vector is integrated into the host cell chromosome, the latter is often sufficient.

Figure 2A:
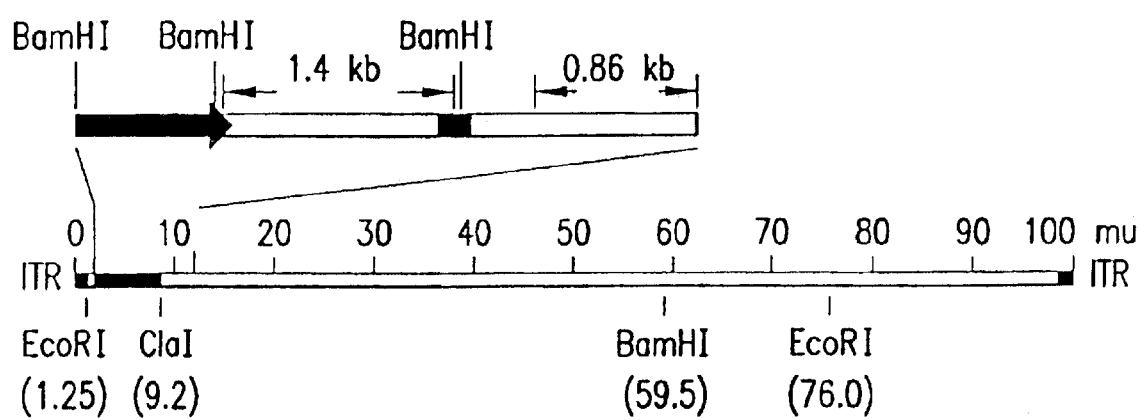
FIG. 2A shows a map used for the structural analysis of Ad5CMV-p53 DNA. A map of Ad5CMV-p53 genomic DNA, with the locations of the p53 expression cassette, the PCR primers, and the restriction sites. The genome size is about 35.4 kb, divided into 100 maps units (1 m.u.=0.35 kb). The p53 expression cassette replaced the E1 region (1.3–9.2 m.u.) of the Ad5 genome. Primer 1 is located in the first intron downstream of the human CMV major IE gene promoter. Primer 2 is located in SV40 early polyadenylation signal. Both of the primers, 15–20 bp away from the p53 cDNA insert at both ends, define a 1.40 kb PCR product. Primers 3 and 4 are located at 11 m.u. and 13.4 m.u. of Ad5 genome, respectively, which define a 0.86 kb viral-genome specific PCR product.

The design and propagation of the preferred p53 adenovirus is diagramed in FIG. 1. In connection with this, an improved protocol has been developed for propagating and identifying recombinant adenovirus (discussed below). After identification, the p53 recombinant adenovirus was structurally confirmed by the PCR analysis, as indicated in FIG. 2. After isolation and confirmation of its structure, the p53 adenovirus was used to infect human lung cancer cell line H358, which has a homozygous p53 gene deletion. Western blots showed that the exogenous p53 protein was expressed at a high level (FIG. 4 and FIG. 5) and peaked at day 3 after infection (FIG. 6).

Figure 7A:
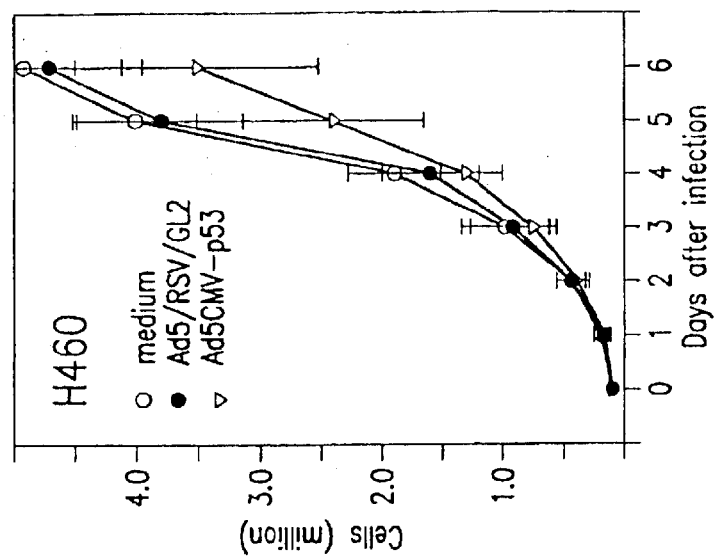
FIG. 7A shows the growth curve of virally-infected human lung cancer cells of cell lines H358. Cells were inoculated at $10^5$ cells per dish (60 mm) and 6 dishes per cell line. After 24 hours, the cells were infected with Ad5CMV-p53 or Ad5/RSV/GL2 at 10 m.o.i. (Multiplicity of infection, i.e., PFU/cell). After infection cells were counted daily for 6 days. The growth curves represent data obtained from 4 separate studies.
Figure 7B:
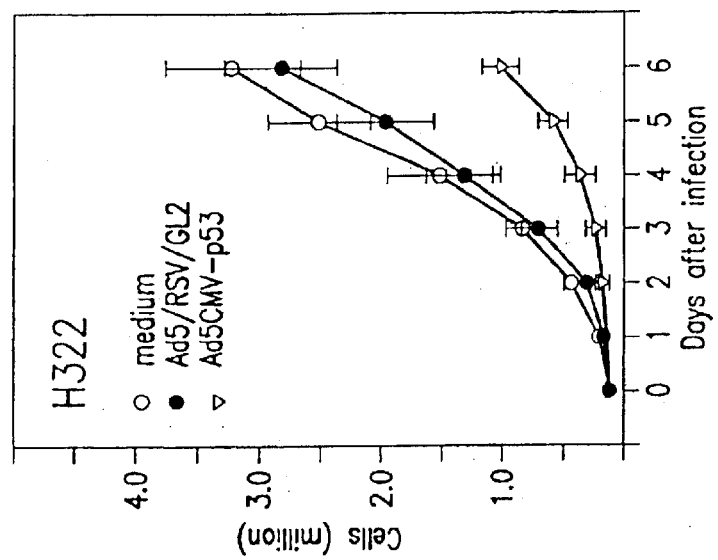
FIG. 7B shows the growth curve of virally-infected human lung cancer cells of cell line H322. Cells were inoculated at 10; cells per dish (60 mm) and 6 dishes per cell line. After 24 hours, the cells were infected with Ad5CMV-p53 or Ad5/RSV/GL2 at 10 m.o.i. (Multiplicity of infection, i.e., PFU/cell). After infection cells were counted daily for 6 days. The growth curves represent data obtained from 4 separate studies.
Figure 7C:
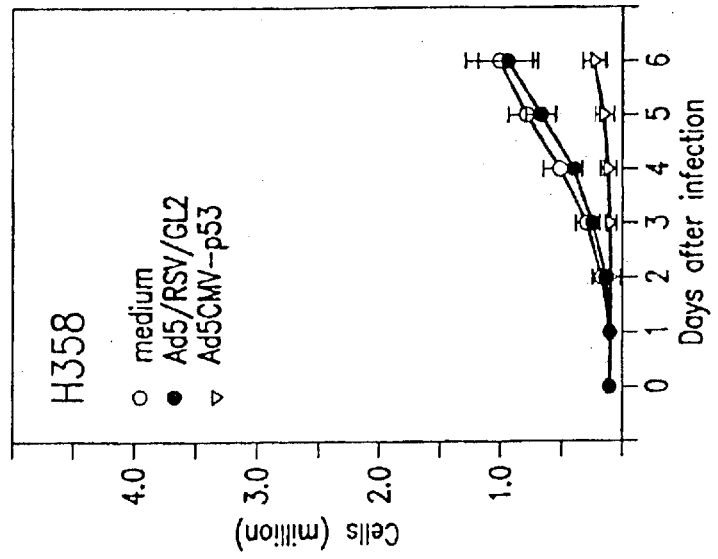
FIG. 7C shows the growth curve of virally-infected human lung cancer cells of cell line H460. Cells were inoculated at $10^5$ cells per dish (60 mm) and 6 dishes per cell line. After 24 hours, the cells were infected with Ad5CMV-p53 or Ad5/RSV/GL2 at 10 m.o.i. (Multiplicity of infection, i.e., PFU/cell). After infection cells were counted daily for 6 days. The growth curves represent data obtained from 4 separate studies.

It was also shown in a p53 point mutation cell line H322 that the mutant p53 was down regulated by the expression of the exogenous p53. As an experimental control, a virion (Ad5/RSV/GL2) that had a structural similarity to that of Ad5CMV-p53 was used. This virion contained a luciferase cDNA driven by Rous sarcoma virus LTR promoter in the expression cassette of the virion. Neither p53 expression nor change in actin expression was detected in cells infected by the virion Ad5/RSV/GL2. Growth of the H358 cells infected with Ad5CMV-p53 was greatly inhibited in contrast to that of noninfected cells or the cells infected with the control virion (FIG. 7A). Growth of H322 cells was also greatly inhibited by the p53 virion (FIG. 7B), while that of human lung cancer H460 cells containing wild-type p53 was less affected (FIG. 7C).

Ad5CMV-p53 mediated a strong inhibitory effect on lung cancer cell growth in vitro. Growth inhibition was not as evident when the cells were infected with Ad5CMV-p53 at MOI lower than 1 PFU/cell, whereas, at MOI higher than 100 PFU/cell, cytotoxicity could be observed even with control virus Ad5/RSV/GL2. In our studies, the optimal dose for growth rate studies was 10–50 PFU/cell. Within this dose range, cell growth inhibition was attributable to the expressed p53 protein.

Tests in nude mice demonstrated that tumorigenicity of the Ad5CMV-p53-treated H3358 cells was greatly inhibited. In a mouse model of orthotopic human lung cancer, the tumorigenic H226Br cells, with a point mutation in p53, were inoculated intratracheally 3 days prior to the virus treatment. Intratracheal instillation of Ad5CMV-p53 prevented tumor formation in this model system suggesting that the modified adenovirus is an efficient vector for mediating transfer and expression of tumor suppressor genes in human cancer cells and that the Ad5CMV-p53 virus may be further developed into a therapeutic agent for use in cancer gene therapy.

Ad3CMV-p53 mediated a high level of expression of the p53 gene in human lung cancer cells as demonstrated by Western blot analysis. Exogenous p53 protein was approximately 14 times more abundant than the endogenous wild-type p53 in H460 cells and about two to four times more abundant than the $\beta$-actin internal control in H358 cells. The high level of expression may be attributed to (1) highly efficient gene transfer, (2) strong CMV promoter driving the p53 CDNA, and (3) adenoviral E1 enhancer enhancing the p53 CDNA transcription. The duration of p53 expression after infection was more than 15 days in H358 cells. However, there was a rapid decrease in expression after postinfection day 5. PCR analysis of the DNA samples from the infected H358 cells showed a decrease of the viral DNA level with the decreased protein level, indicating the loss of viral DNA during the continuous growth of cancer cells in vitro.

The decrease in p53 expression may also have resulted from cellular attenuation of the CMV promoter that controls p53 expression, since the phenomenon of host cell-mediated CMV promoter shut off has been reported previously (Dai, et al., 1992). Adenoviral vectors are nonintegrative gene transfer vectors and therefore the duration of gene expression depends upon a number of factors, including the host cells, the genes transferred, and the relevant promoter. Crystal and co-workers showed low level expression of the cystic fibrosis transmembrane conductance regulator gene in cotton rat epithelial cells was detectable 6 weeks after infection (Rosenfeld, et al., 1992). Perricaudet's laboratory demonstrated minimal expression of minidystrophin gene in mdx mouse muscle lasted for more than 3 months after infection. The short-term high level expression of the wild-type p3; protein observed in the present study may have the beneficial effect of reducing possible side effects on normal cells following in vivo treatment with Ad5CMV-p53.

The studies disclosed herein indicate that the p53 recombinant adenovirus possesses properties of tumor suppression, which appear to operate by restoring p53 protein function in tumor cells. These results provide support for the use of the Ad5CMV-p53 virion as a therapeutic agent for cancer treatment.

F. Improved Protocol for Propagating and Identifying Recombinant Adenovirus

Recombinant adenovirus as a new gene delivery system has many potential applications in gene therapy and vaccine development. Propagation of recombinant adenovirus is therefore an important molecular biological tool. The existing methods for propagating recombinant adenovirus use calcium phosphate precipitation-mediated transfection into 293 cells and subsequent plaque assays on the transfected cells. The transfection efficiency associated with this method needs to be improved and, also, the procedure could be simplified.

Prior to the present invention, propagation of recombinant adenovirus was conventionally carried out by calcium phosphate-mediated transfection. This procedure involves exposing cells to vector or plasmid DNA in calcium phosphate for several hours prior to a brief shock treatment, e.g., one minute in 15% glycerol. This methods suffers from the significant drawback of resulting in only low levels of DNA being incorporated into the cell, i.e., it is a very inefficient means of transfection. Viral propagation was also normally indicated by the appearance of plaques which are observed as clear, round areas around lysed cells indicating cell lysis caused by virus propagation.

The inventors have developed a novel procedure for producing adenovirus which significantly improves the transfection efficiency and also simplifies selection. The inventors have discovered that a combination of liposome-mediated transfection, such as DOTAP-mediated transfection, with the observation of cytopathic effect (CPE) leads to both improved efficiency and rapid and simplified detection. In the new procedure, liposome DOTAP-mediated gene transfer is used to transduce an expression vector and recombination plasmid into 293 cells. The transfected cells, instead of being overlaid with 0.5% agarose for plaque assays, are then maintained continually in MEM medium for observation of cytopathic effect (CPE).

In two studies using the new method, 2 wells out of a 24-well plate and 3 dishes out of five 60-mm dishes generated CPE at days 10 and 12 after cotransfection, respectively. In contrast, using the calcium-phosphate precipitation method, no recombinant virus was obtained in three trials from the cotransfection with twenty 60-mm dishes in each experiment. Using CAT assays in Hep G2 and HeLa cell lines, DOTAP-mediated transfection resulted in 5 fold higher CAT activity than calcium phosphate transfection.

Elimination of the agarose overlay after cotransfection also simplified the procedure. The endpoint of the study, propagation of virus, becomes much more simple and clear by directly observing the CPE instead of identifying plaques, which is usually unclear and difficult to determine after 10–14 day incubation. FIG. 3 shows the cell culture with CPE in comparison with the cell culture without CPE.

The inventors have also developed a rapid technique to determine adenovirus titers using PCR. The direct PCR analysis of DNA samples from the supernatant of the cell cultures with CPE conveniently uses two pairs of primers, one to amplify insert-specific and the other to amplify viral genome-specific sequences. The inventors have shown that adenoviruses released into the cell culture medium are detectable by PCR, thereby allowing one to use as little as about 50 µL of supernatant to prepare DNA templates.

Identification of the insert-specific and viral genome-specific DNA sequences resulting from PCR amplification may be determined by, or example, analysis of PCR amplified products on agarose gels. Bands corresponding to insert-specific DNA and viral genome-specific DNA, and also the primers, may be identified by comparison with the appropriate standard markers.

Where PCR is employed to amplify insert-specific and viral genome-specific gene products, one will first prepare a primer specific for the sequences to be amplified. Efficient and selective amplification is achieved by employing two primer pairs: one to amplify a defined section of the insert-specific product, and the other to define a segment of the viral genome-specific product. By way of example only, a cassette for expression of p53 has been constructed with a human cytomegalovirus (CMV) promoter and SV40 early polyadenylation signal. The first primer set will include a primer located in the first intron downstream of the human CMV major IE gene promoter while the other primer of the first primer set will be located in SV40 early polyadenylation signal. Ideally, both of these primers are 15 to 20 base pairs away from the cDNA insert which, in the illustrative example, is p53.

A defined PCR product should be selected, for example a 1.40 kb p53 cDNA. As an example, the second set of primers may be located at 11 M.U. and 13.4 M.U. of the Ad5 genome to define a 0.86 kb viral genome specific PCR product.

Primer selection is well known to those of skill in the art. One may construct primers for amplification of selected portions to DNA sequences whose base pair sequence is known. Primers hybridize to DNA and serve as initiation sites for synthesis of a portion of the gene. Nucleotide primers are designed to bind at separate sites on opposing duplex strains thereby defining the intervening sequence as the portion to be amplified. Nucleic acid molecules to be employed as primers will generally include at least a 10 base pair sequence which will be complementary to the DNA segment one desires to amplify. The 10 base pair size is selected as a general lower limit in that sizes smaller than 10 bases may not effectively hybridize and stabilization may become a problem. Preferably, sizes of 15–20 are utilized and in a preferred aspect of the invention the primer pairs shown in FIG. 1 are employed where size is 19 or 20 base pairs.

G. Patients and Treatment Protocols

The inventors propose that the regional delivery of adenoviral-p53 gene constructs to lung cancer cells in patients with p53-linked cancers, such as unresectable obstructing endobronchial cancers, will be a very efficient method for delivering a therapeutically effective gene to counteract the clinical disease. It is proposed that this approach is a significant improvement on current cancer therapies which rely on attempts to kill or remove the last cancer cell. As tumor cell dormancy is an established phenomenon, this makes effective killing highly unlikely.

It is anticipated that the uptake of the adenovirus constructs by NSCLC cells will decrease the rate of proliferation of these cells. This would increase the length of time the affected lung would remain expanded, prevent regrowth of the endobronchial tumor, and prolong the patient's survival.

Patients with unresectable endobronchial tumor recurrence that is partially or completely obstructing the airway and that have failed or are unable to receive external beam radiotherapy will be considered for this protocol. Existing therapies for this condition offer only short-term palliation. Most patients have recurred despite external beam radiotherapy. It may be possible to insert a brachytherapy catheter and administer additional radiotherapy Patients receiving this treatment have a median survival of 6 months. Patients failing brachytherapy would also be eligible to receive gene therapy. Tumor can be removed from the airway with the laser or biopsy forceps. This can be done in conjunction with injection of the adenoviral constructs thus decreasing the volume that must be injected. The administration of the viral constructs would not preclude the patient from receiving other palliative therapy if the tumor progresses.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Construction of p53 Expression Vector

This example describes the construction of a p53 expression vector. This vector is constructed as indicated and is used to replace the E1 region (1.3–9.2 m.u.) of the Adenovirus strain Ad5 genome and employed to construct the Adenovirus virion described in Example 2.

The p53 expression cassette shown in FIG. 1, which contains human cytomegalovirus (CMV) promoter (Boshart, et al., 1985), p53 cDNA, and SV40 early polyadenylation signal, was inserted between the Xba I and Cla I sites of pXCJL1 (provided by Dr. Frank L. Graham, McMaster University. Canada).

The genome size is about 35.4 kb, divided into 100 map units (1 m.u.=0.35 kb). The p53 expression cassette replaced the E1 region (1.3–9.2 m.u.) of the Ad5 genome.

Primer 1 has the sequence 5'-GGCCCACCCCCTTGGCTTC-3' (SEQ ID NO: 1) and is located in the first intron downstream of the human CMV major IE gene promoter (Boshart, et al., 1985). Primer 2 has the sequence 5'-TTGTAACCATTATAAGCTGC-3' (SEQ ID NO:2) and is located in SV40 early polyadenylation signal. Both of the primers, 15–20 bp away from the p53 cDNA insert at both ends, define a 1.40 kb PCR product. Primer 3 has the sequence 5'-TCGTTTCTCAGCAGCTGTTG-3' (SEQ ID NO:3) and primer 4 has the sequence 5'-CATCTGAACTCAAAGCGTGG-3'(SEQ ID NO:4) and are located at 11 m.u. and 13.4 m.u. of the Ad5 genome, respectively, which define a 0.86 kb viral-genome specific PCR product.

EXAMPLE 2

Generation and Propagation of Recombinant p53 Adenovirus

This example describes one method suitable for generating helper-independent recombinant adenoviruses expressing p53. The molecular strategy employed to produce recombinant adenovirus is based upon the fact that, due to the packaging limit of adenovirus, pJM17 cannot form virus on its own. Therefore, homologous recombination between the p53 expression vector plasmid and pJM17 within a transfected cell results in a viable virus that can be packaged only in cells which express the necessary adenoviral proteins.

The method of this example utilizes 293 cells as host cells to propagate viruses that contain substitutions of heterologous DNA expression cassettes at the E1 or E3 regions. This process requires cotransfection of DNA into 293 cells. The transfection largely determines efficiency of viral propagation. The method used for transfection of DNA into 293 cells prior to the present invention was usually calcium-phosphate/DNA coprecipitation (Graham and van der Eb, 1973). However, this method together with the plaque assay is relatively difficult and typically results in low efficiency of viral propagation. As illustrated in this example, transfection and subsequent identification of infected cells were significantly improved by using liposome-mediated transfection, when identifying the transfected cells by cytopathic effect (CPE).

The 293 cell line was maintained in Dulbecco's modified minimal essential medium supplemented with 10% heat-inactivated horse serum. The p53 expression vector and the plasmid pJM17 (McGrory, et al., 1988) for homologous recombination were cotransfected into 293 cells by DOTAP-mediated transfection according to the manufacture's protocol (Boehinger Mannheim Biochemicals, 1992). This is schematically shown in FIG. 1.

The 293 cells (passage 35, 60% confluency) were inoculated 24 hours prior to the transfection in either 60 mm dishes or 24-well plates. The cells in each well were tranfected with: 30 $\mu$l DOTAP, 2 $\mu$g of p53 expression vector, and 3 $\mu$g of plasmid pJM17. After transfection cells were fed with the MEM medium every 2–3 days until the onset of CPE.

EXAMPLE 3

Confirming the Identity of Recombinant Adenovirus

This example illustrates a new polymerase chain reaction (PCR) assay for confirming the identity of recombinant virions following cotransfection of the appropriate cell line.

Aliquots of cell culture supernatants (50 to 370 $\mu$l) were collected from the test plates, treated with proteinase K (50 $\mu$g/ml with 0.5% SDS and 20 mM EDTA) at 56° C. for 1 hour, extracted with phenol-chloroform, and the nucleic acids were ethanol precipitated. The DNA pellets were resuspended in 20 $\mu$l dH$_2$O and used as template for PCR amplification. The relative locations of the PCR primers and their sequences are depicted in FIG. 1 and are SEQ ID NOS: 1, 2, 3 and 4, respectively. The cDNA insert-specific primers define a 1.4 kb PCR product and the viral genome-specific primers define a 0.86 kb PCR product. The PCR reactions were carried out in a 50 $\mu$l volume containing 4 mM MgCl$_2$, 50 mM KCl, 0.1% triton X-100, 200 $\mu$M each of dNTPs, 10 mM Tris-Cl (pH 9.0), 2 $\mu$M of each primer, and 1.0 unit of Taq polymerase (Promega). The reactions were carried out at 94° C., 0.5 min, 56° C., 0.5 min, and 72° C., 1 min for 30 cycles.

In order to simplify the procedure of identification of newly propagated recombinant virus, a direct PCR assay on DNA samples from cell culture supernatant was developed. Aliquots (50 or 370 $\mu$l) of the cell medium supernatant with CPE were treated with proteinase K and phenol/chloroform extraction. After ethanol precipitation, the DNA samples were analyzed using PCR employing two pairs of primers to amplify insert-specific and viral-genome-specific sequences. The PCR primer targets and their sequences are depicted in FIG. 1. Primers 1, 2, 3 and 4 are represented by SEQ ID NOS: 1, 2, 3 and 4, respectively.

Figures 2B, 2C:
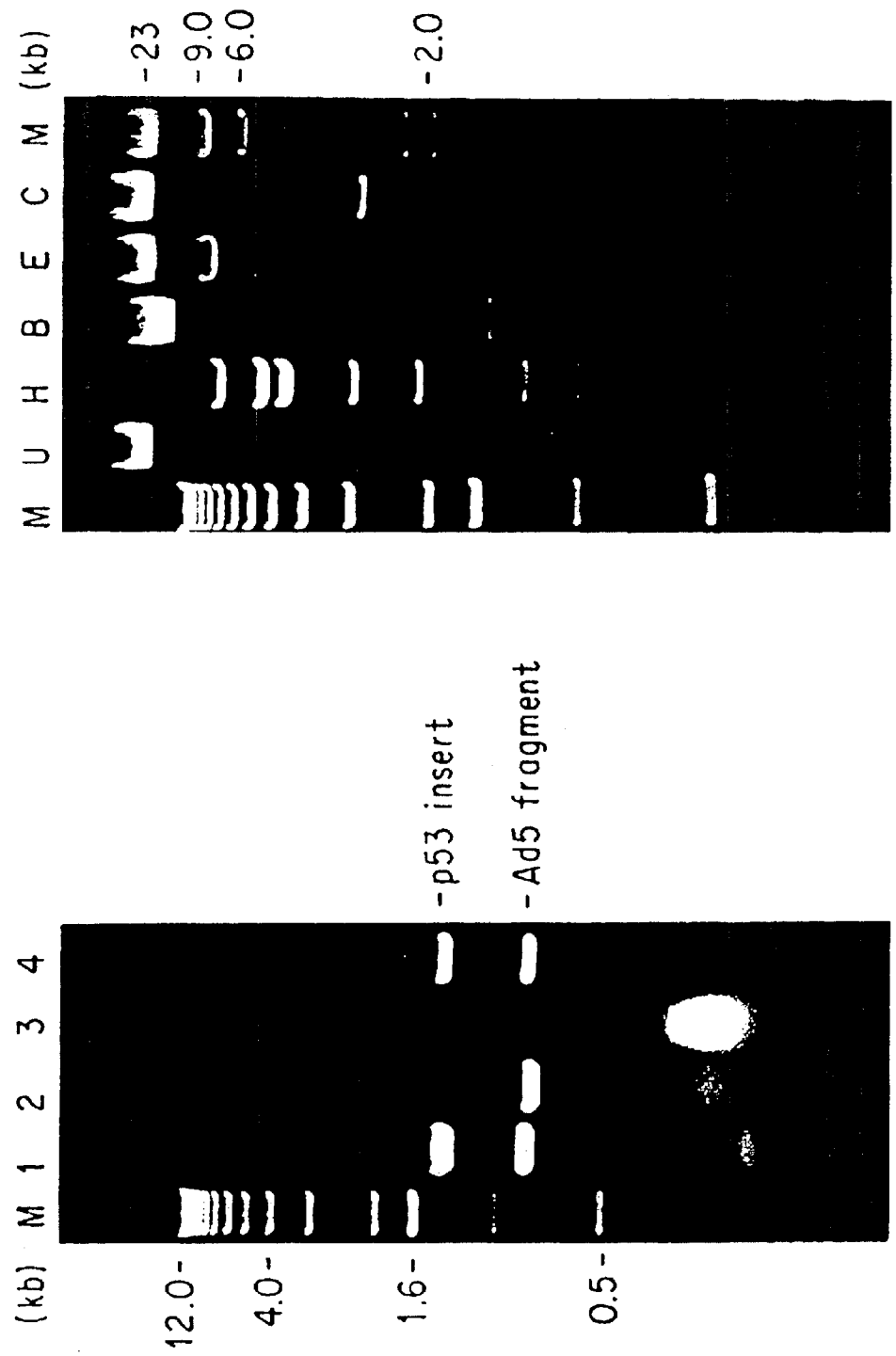
FIG. 2B shows agarose gel analysis of PCR products. Two pairs of primers that define 1.4-kb (p53) and 0.86-kb (Ad5) DNA fragments were used in each reaction. DNA templates used in each reaction were pEC53 plasmid (lane 1), Ad5/RSV/GL2 DNA (lane 2), no DNA (lane 3), and Ad5CMV-p53 DNA (lane 4). The lane labeled (M) corresponds to molecular weight markers.
FIG. 2C shows restriction mapping of Ad5CMV-p53 DNA. CsCl-gradient purified Ad5CMV-p53 DNA samples were digested with no enzyme (U), Hind III (H), Bam HI (B). Eco RI (E), and Cla I (C), respectively, and analyzed on 1% agarose gel. The lanes labeled (M) are molecular weight markers.
Figure 3B:
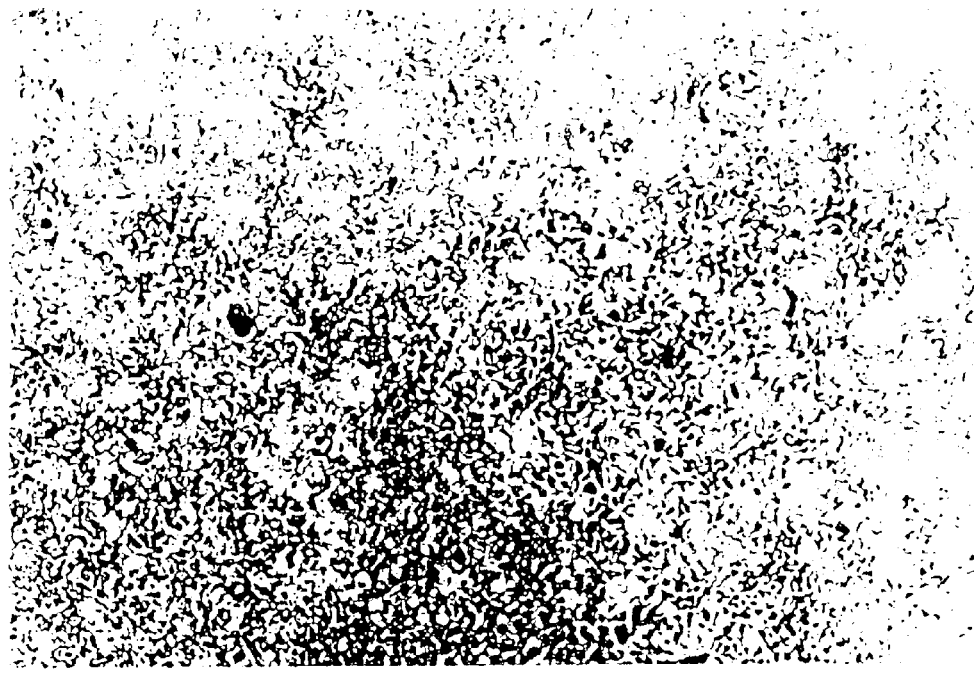
FIGS. 3A, 3B, 3C and 3D, observation of cytopathic effects on 293 by recombinant adenovirus.
Figure 3A:
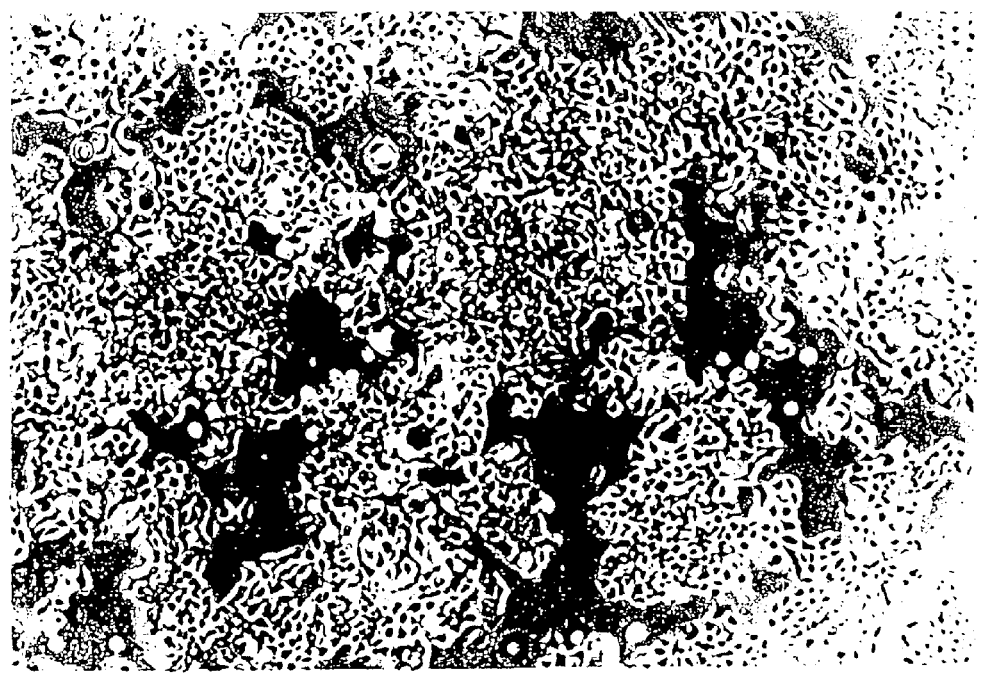
Figure 3D:
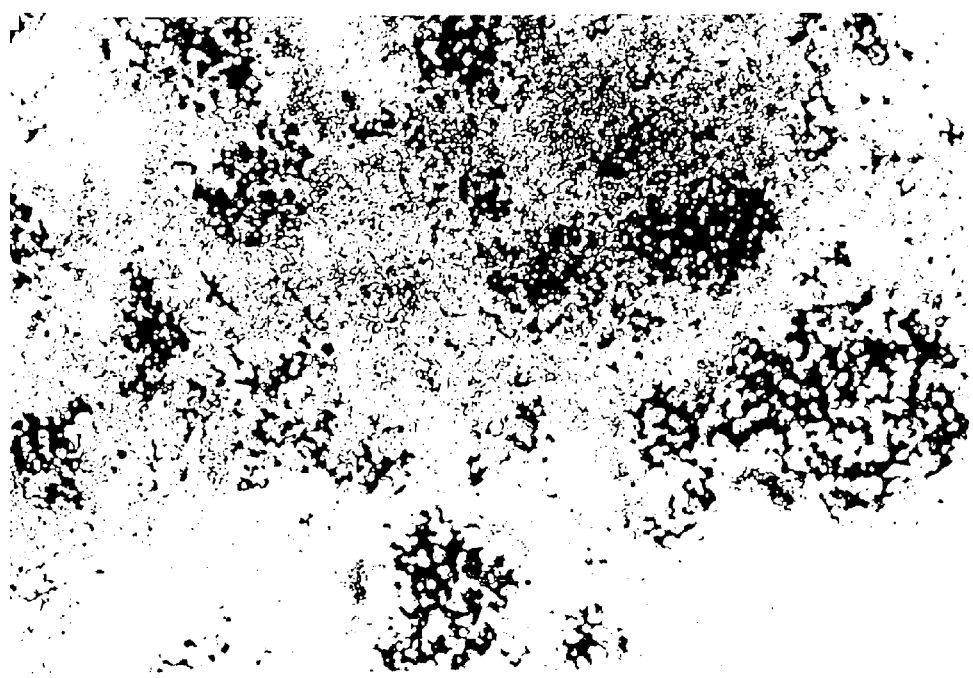
Figure 3C:
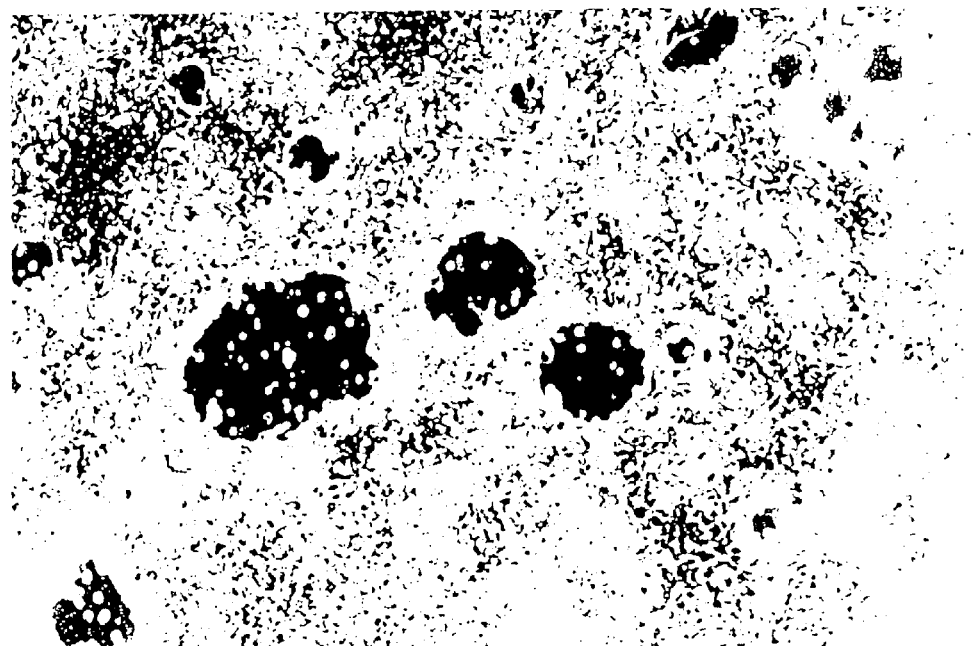
Figure 4A:
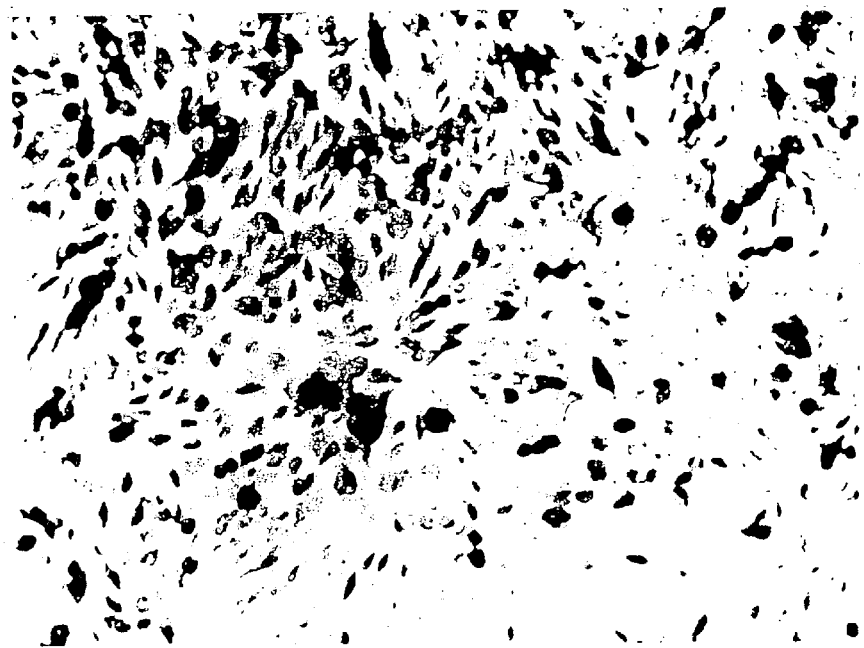
FIGS. 4A, 4B, 4C and 4D are a series of immunohistological images of H358 cells.
Figure 4B:
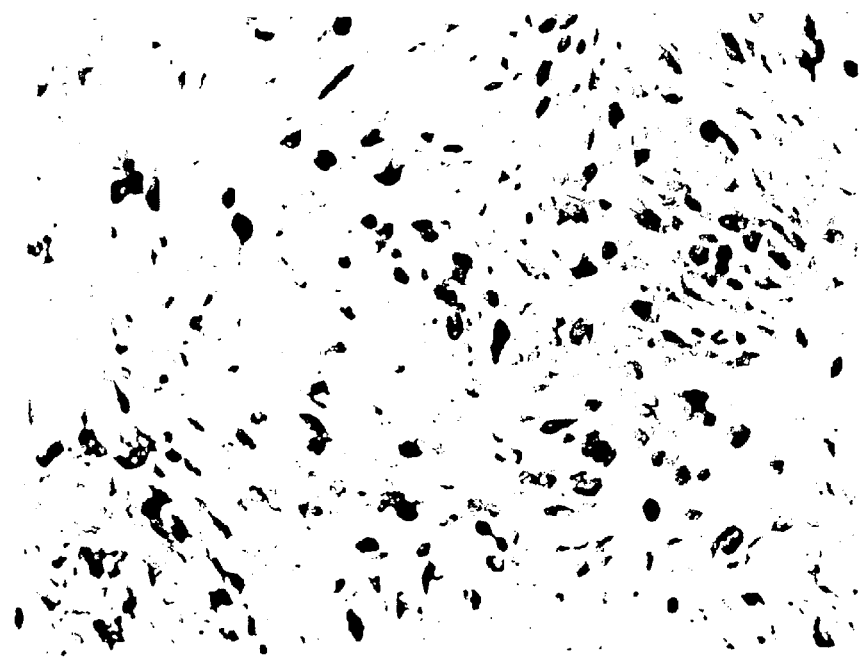
Figure 4C:
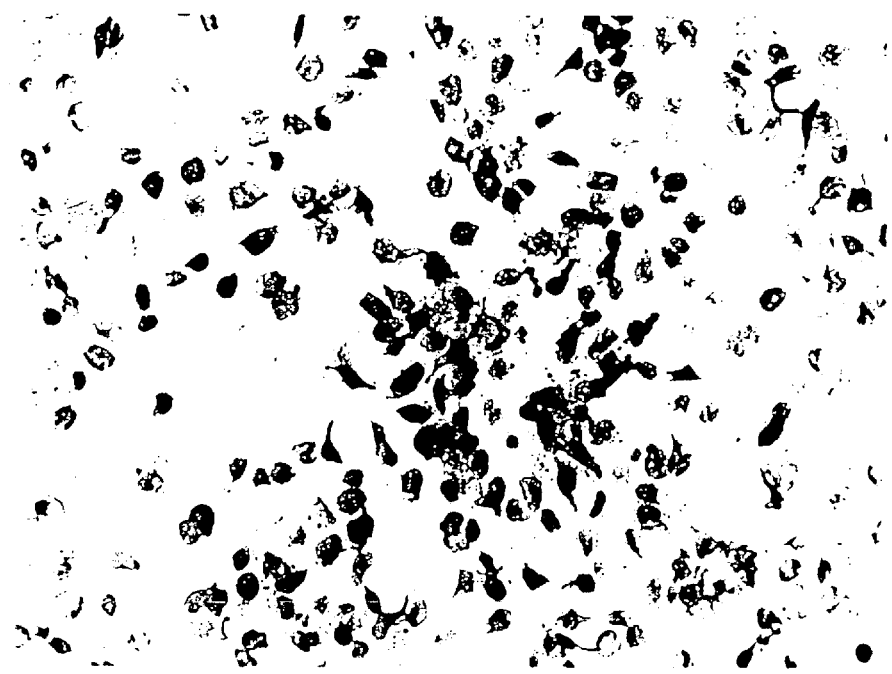
Figure 4D:
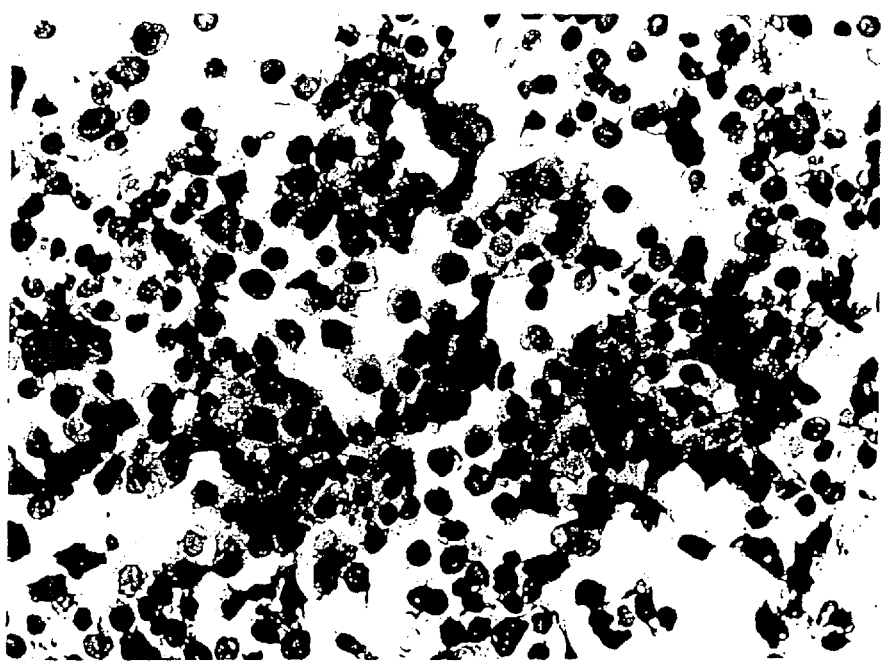

As a result, a 1.4 kb cDNA insert and a 0.86 kb viral genome fragment were amplified from the expression vector (positive control) and the DNA samples of the positive cell culture (FIG. 2B, lane 1 and 4, respectively.). Only the 0.86 kb fragment was amplified from the DNA sample of Ad5/RSV/GL2 virus (negative control, lane 2). No amplified bands appeared from PCR reactions that used either untreated positive cell culture medium supernatant (lane 3).

These results indicated that adenoviruses released into cell culture medium are detectable by PCR, using as little as 50 μL of the cell culture medium supernatant for preparing DNA templates. These results will allow development of a quantitative method for using this technique to determine adenovirus titers, traditionally done by plaque assays.

The wild-type sequence of the p53 cDNA in the Ad5CMV-p53 virus was confirmed by dideoxy DNA sequencing on the CsCl-gradient-purified viral DNA. The control virus Ad5/RSV/GL2, generated in a similar manner, has a structure similar to that of Ad5CMV-p53 except a Rous sarcoma viral promoter and luciferase cDNA were used in its expression cassette. The recombinant adenovirus that carries a E. coli b-galactosidase gene (LacZ), Ad5CMV-LacZ, also has a structure similar to that of Ad5CMV-p53, and was obtained from Dr. Frank L. Graham.

Viral stock, titer, and infection. Individual clones of the Ad5CMV-p53, Ad5/RSV/GL2, and Ad5CMV-LacZ viruses were obtained by plaque-purification according to the method of Graham and Prevec (1991). Single viral clones were propagated in 293 cells. The culture medium of the 293 cells showing the completed cytopathic effect was collected and centrifuged at 1000×g for 10 min. The pooled supernatants were aliquoted and stored at −20° C. as viral stocks. The viral titers were determined by plaque assays (Graham and Prevec, 1991). Infections of the cell lines were carried out by addition of the viral solutions (0.5 ml per 60-mm dish) to cell monolayers and incubation at room temperature for 30 min with brief agitation every 5 min. This was followed by the addition of culture medium and the return of the infected cells to the 37° C. incubator.

The gene transfer efficiency of the recombinant adenoviruses was also evaluated using Ad5CMV-LacZ in a variety of cell lines such as H226Br, H322, H460, HeLa, Hep G2, LM2, and Vero. By X-gal staining, all of the cell lines were stained 97–100% blue after infection with Ad5CMV-LacZ at an MOI of 30 PFU/cell.

EXAMPLE 4

Ad5CMV-p53-Directed p53 Gene Expression in Human Lung Cancer Cells

This example describes the use of recombinant p53 adenovirus to infect human lung cancer cells with a homozygous p53 gene deletion. The results show that growth of these cells and expression of mutant p53 was suppressed, indicating the potential of the Ad5CMV-p53 virion as a useful agent for control of metastatic cells.

Immunohistochemistry was performed on infected cell monolayers that were fixed with 3.8% formalin and treated with 3% $H_2O_2$ in methanol for 5 min. Immunohistochemical analysis was performed using Vectastain Elite kit (Vector, Burlingame, Calif.). The primary antibody used was anti-p53 antibody PAb 1801 (Oncogene Science, Manhasset, N.Y.); MOPC-21 (Organon Teknika Corp., West Chester, Pa.) was used as a negative control. The second antibody was an avidin-labeled anti-mouse IgG (Vector). The biotinylated horseradish peroxidase ABC complex reagent was used to detect the antigen-antibody complex. Finally the cells were counterstained with Harris hematoxylin (Sigma) and mounted with Cytoseal 60 (Stephens Scientific, Riverdale, N.J.).

Immunohistochemical analysis of the infected cell lines was performed to examine the in situ expression of p53 expression driven by the CMV promoter of the Ad5CMV-53 virus. In the H358 cell line, which has a homozygous deletion of p53, the p53 gene was transferred with 97–100% efficiency, as detected by immunohistochemical analysis, when the cells were infected with Ad5CMV-p53 at a multiplicity of infection of 30–50 plaque-forming units (PFU)/cell (FIG. 4).

The high transfer efficiency of recombinant adenovirus was confirmed by Ad5CMV-LacZ, a virus which carries the LacZ gene transcribed by the human CMV IE promoter. At an MOI of 30–50 PFU/cell, all of the cells examined, including HeLa, Hep G2, LM2, and the human NSCLC cancer cell lines were 97–100% positive for b-galactosidase activity by X-gal staining. These results indicate that adenoviral vectors are an efficient vehicle for gene transfer into human cancer cells.

Western blotting analysis was performed on total cell lysates prepared by lysing monolayer cells in dishes with SDS-PAGE sample buffer (0.5 ml per 60-mm dish) after rinsing the cells with phosphate-buffered saline (PBS). For SDS-PAGE analysis lanes were loaded with cell lysates equivalent to $5 \times 10^4$ cells (10–15 ml). The proteins in the gel were transferred to Hybond™-ECL membrane (Amersham, Arlington Heights, Ill.). The membranes were blocked with 0.5% dry milk in PBS and probed with the primary antibodies: mouse anti-human p53 monoclonal antibody PAb 1801 and mouse anti-human β-actin monoclonal antibody (Amersham), washed and probed with the secondary antibody: horseradish peroxidase-conjugated rabbit anti-mouse IgG (Pierce Chemical Co., Rockford, Ill.). The membranes were developed according to the Amersham's enhanced chemiluminescence protocol. Relative quantities of the exogenous p53 expressed were determined by densitometer (Molecular Dynamics Inc., Sunnyvale, Calif.).

Figure 5A:
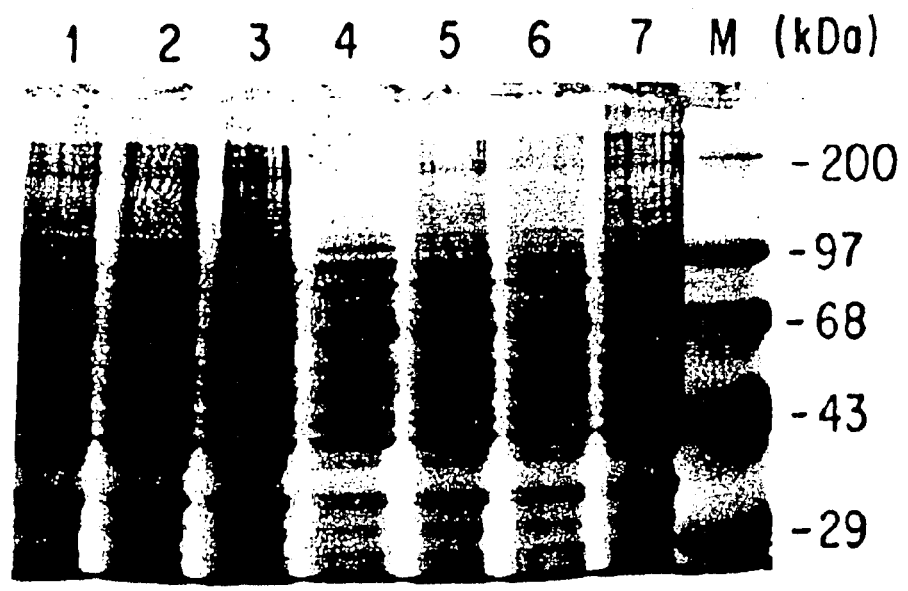
FIG. 5A shows a Coomassie-blue stained SDS-PAGE gel comparing the relative level of expression of exogenous p53 in H358 cells. H358 cell samples that were infected with Ad5CMV-p53 or Ad5!RSV/GL2 at 30 PFU/cell were prepared 24 and 72 h after infection. Coomassie blue staining of an SDS-PAGE analysis, showing relative quantities of protein samples loaded. Lanes 1 and 4 contain the samples of the Ad5/RSV/GL2-infected cells. Lanes 2 and 3 contain the samples of the cells infected with two individual stocks of Ad5CMV-p53 at 24 h after infection. Lanes 5 and 6 are the Ad5CMV-p53-infected cell samples collected at 72 h after infection. Lane 7 is mock-infected H358 sample 72 h after infection. Lane M, prestained molecular weight markers in kDa (GIBCO-BRL).
Figure 5B:
FIG. 5B shows a Western blot analysis of the identical lane setting gel as that of the SDS-PAGE in FIG. 5A. The relative levels of expression of p53 were analyzed by Western blotting using anti-p53. Primary antibodies used were monoclonal antibodies against p53 protein (PAb 1801, Oncogene Science Inc.) and β-actin (Amersham Inc.). The HRP-conjugated second antibody and ECL developer were from Amershem Inc. viral-infected H358 cells by Western Blotting. Western blot of FIG. 5B have an equivalent setup and order to those in FIG. 5A.
Figure 6:
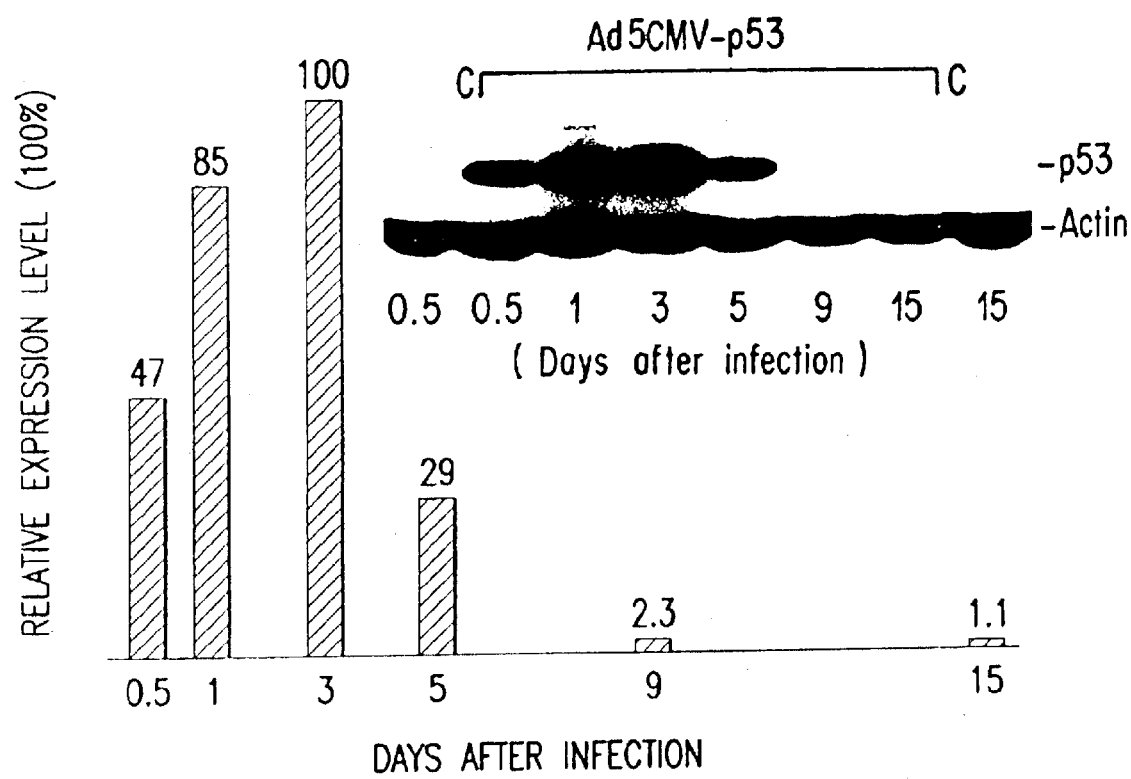
FIG. 6 is a time course of the p53 expression, determined by Western blotting. Multiple dishes of H358 cells were infected with Ad5CMV-p53 at 10 PFU/cell. Cell lysates were prepared at indicated time points after infection. Western blotting was probed with anti-p53 and anti-actin antibodies simultaneously. The lanes designated 'C' represent negative controls. The histogram represents the relative quantities of p53 as determined by a densitometer.

Western blots showed the exogenous p53 protein was expressed at a high level (FIG. 5A lanes 2,3 and 5,6). The protein peaked at day 3 after infection (FIG. 6, insert, 0.5 days to 3 days). As a control, a virion with a structure similar to the recombinant Ad5CMV-p53 of Example 1 was constructed. This virion contains a luciferase cDNA driven by Rous Sarcoma Virus LTR promoter in the expression cassette of the virion. Neither p53 expression nor change in actin expression was detected in the cells infected by the virion Ad5/RSV/GL2.

The recombinant p53 adenovirus was used to infect three human lungs NSCLC cell lines: cell line H358, which has a homozygous deletion of the p53 gene, cell line H322, which has a point mutation of the p53 gene at codon 248 (G to T), and cell line H460, which has a wild-type p53 gene. The growth rate of human NSCLC cells was determined following the inoculation of H322 and H460 ($1 \times 10^5$) or H358 ($2 \times 10^5$) in 60-mm culture dishes 24 h before viral infection. The cells were infected with the viruses at a multiplicity of infection (MOI) of 10 PFU/cell. Culture medium was used for the mock infection control. Triplet cultures of each cell line with different treatments were counted daily for days 1–6 after infection.

Growth of the H358 cells infected with Ad5CMV-p53 was greatly inhibited in contrast to that of noninfected cells or the cells infected with the control virion (FIG. 7A). Growth of H322 cells was also greatly inhibited by the p53 virion (FIG. 7B), while that of human lung cancer H460 cells containing wild type p53 was affected to a lesser degree (FIG. 7C). Growth of the Ad5CMV-p53 virus-infected H358 cells was inhibited 79%, whereas that of noninfected cells or the cells infected with the control virus were not inhibited. Growth of cell line H322, which has a point mutation in p53, was inhibited 72% by Ad5CMV-p53, while that of cell line H460 containing wild-type p53 was less affected (28% inhibition).

The results indicate that the p53 recombinant adenovirus possesses properties of tumor suppression, working through restoration of the p53 protein function in tumor cells.

EXAMPLE 5

Ad5CMV-p53 in the Treatment of p53 Deficient Cells

The present example concerns the use of recombinant p53 adenovirus to restore growth suppression of tumor cells in vitro and thus to treat the malignant or metastatic growth of cells. It describes some of the ways in which the present invention is envisioned to be of use in the treatment of cancer via adenovirus-mediated gene therapy.

H358 cells were infected with Ad5CMV-p53 and Ad5/RSV/GL2 at a MOI of 10 PFU/cell. An equal amount of cells were treated with medium as a mock infection. Twenty-four hours after infection, the treated cells were harvested and rinsed twice with PBS. For each treatment, three million ($3 \times 10^6$) cells in a volume of 0.1 ml were injected s.c. to each nude mouse (Harlan Co., Houston, Tex.). Five mice were used for each treatment. Mice were irradiated (300 cGy, $^{60}$Co) before injection and examined weekly after injection. Tumor formation was evaluated at the end of a 6-week period and tumor volume was calculated by assuming a spherical shape with the average tumor diameter calculated as the square root of the product of cross-sectional diameters.

To determine the inhibitory effect on tumorigenicity mediated by Ad5CMV-p53 nude mice were injected s.c. with H358 cells (a human NSCLC-type cell) to induce neoplastic growth. Each mouse received one injection of cells that had been infected with Ad5CMV-p53 or Ad5/RSV/GL2 at 10 PFU/cell for 24 h. H358 cells treated with medium alone were used as mock-infected controls. Tumors, first palpable at postinjection day 14, were induced only by the mock- or control virus-infected cells as demonstrated in Table I:

TABLE I

Effect of Ad5CMV-p53 on tumorigenicity of H358 in nude mice[a]

| Treatment | No. of Tumors/ No. of Mice (%) | Mean Volume ($mm^3 \pm SD$) |
|---|---|---|
| Medium | 4/5 (80) | 37 ± 12 |
| Ad5/RSV/GL2 | 3/4 (75) | 30 ± 14 |
| Ad5CMV-p53 | 0/4 (0) | — |

[a]The treated H358 cells were injected s.c. at $2 \times 10^6$ cells/mouse. Tumor sizes were determined at the end of a 6-week period.

As shown in Table I mice that received Ad5CMV-p53-treated cells did not develop tumors. The tumors at the end of a 6-week period were 4–10 mm in diameter. This study was initiated with five mice per group: one mouse each in the Ad5CMV-p53 or Ad5/RSV/GL2 group failed to complete the study. The early deaths were presumably due to nosocomial infection.

EXAMPLE 6

Ad5CMV-p53 in the Treatment of Lung Cancer

The present example concerns the use of recombinant p53 adenovirus to restore growth suppression of tumor cells in vivo and thus to treat cancers in animals. It describes some of the ways in which the present invention is envisioned to be of use in the treatment of cancer via adenovirus-mediated gene therapy.

The efficacy of Ad5CMV-p53 in inhibiting tumorigenicity was further evaluated in the mouse model of orthotopic human lung cancer. Since H358 and H322 cells did not produce tumors in this model, cell line H226Br was used. This cell line has a squamous lung cancer origin and metastasized from lung to brain. H226br has a point mutation (ATC to GTC) at exon 7, codon 254, of the p53 gene and is tumorigenic in mice.

The procedure for tests in the mouse model of orthotopic human lung cancer has been previously described (Georges, et al., 1993). Briefly, nude mice treated with radiation (300 cGy, $^6$Co) were inoculated with H226Br cells by intratracheal instillation. Each mouse received $2 \times 10^6$ cells in a volume of 0.1 ml PBS. Three days after inoculation, 10 mice per group were treated with 0.1 ml of viruses or vehicle (PBS) by intratracheal instillation once a day for two days. The virus dosage used was $5 \times 10^7$ Ad5CMV-p53 or Ad5/RSV/GL2 per mouse. The mice were euthanized at the end of a 6-week period. Tumor formation was evaluated by dissecting the lung and mediastinum tissues and measuring the tumor size. The tumors were confirmed by histologic analysis of the sections of the tumor mass.

Figure 8:
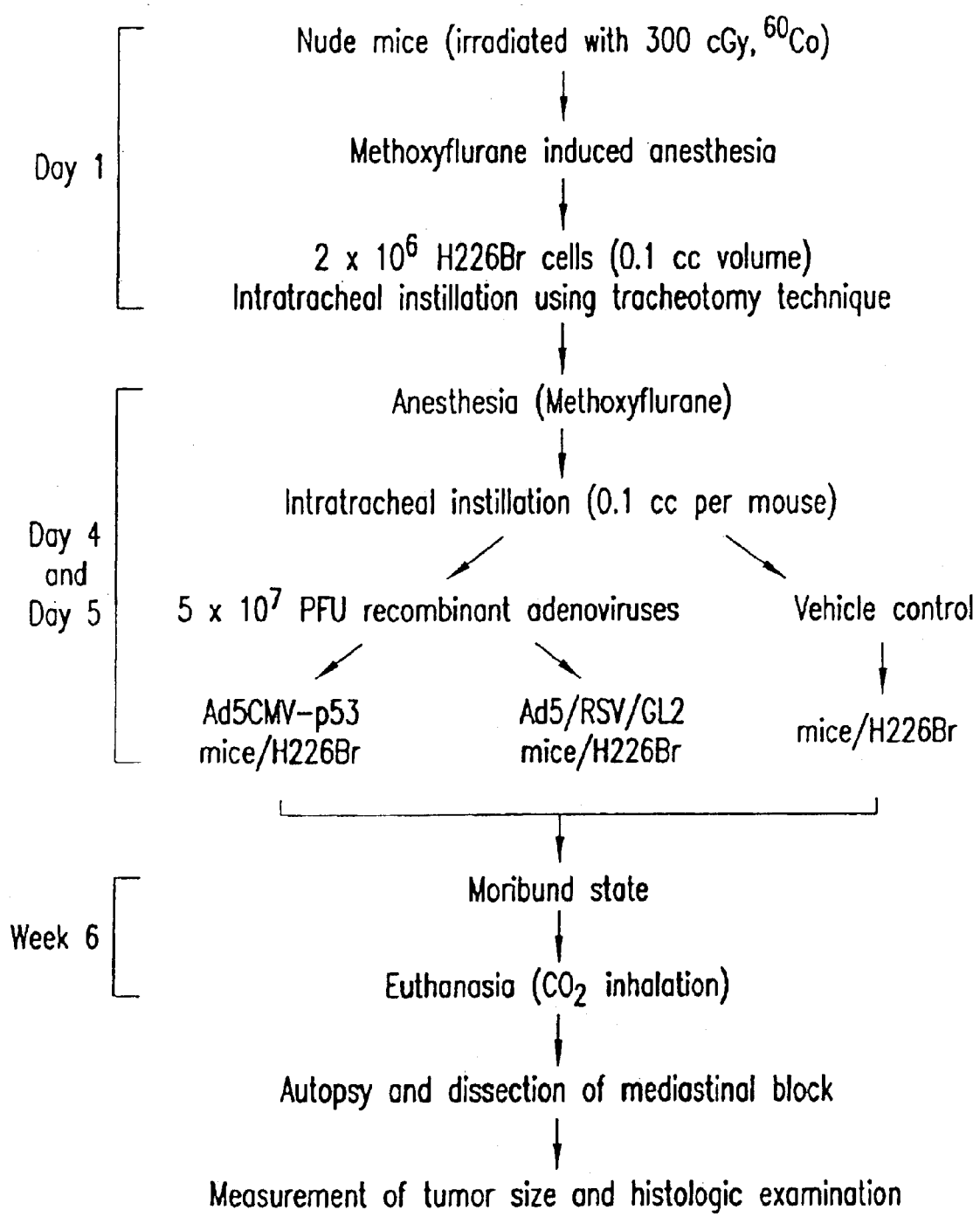
FIG. 8 shows a flow chart of tests of Ad5CMV-p53 in orthotopic lung cancer model. The dosages and schedule of treatment of nude mice innoculated with H226Br cells and viruses are summarized in the flow chart.
Figure 9A:
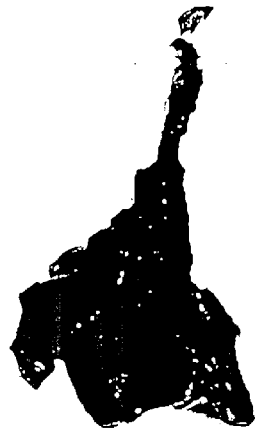
FIGS. 9A, 9B, 9C, and 9D are samples of the lung and mediastinum dissection from treated and control mice.
Figure 9B:
Figure 9C:
Figure 9D:
Figure 9D:

The irradiated nude mice were inoculated with $2 \times 10^6$ H226Br cells/mouse by intratracheal instillation. Three days after inoculation, each of the mice (8–10 mice per group) were treated with 0.1 ml of either Ad5CMV-p53 or Ad5/RSV/GL2 or vehicle (PBS) by intratracheal instillation once a day for two days. The virus dosage used was $5 \times 10^7$ PFU/mouse. Tumor formation was evaluated at the end of a 6-week period by dissecting the lung and mediastinum tissues and measuring the tumor size. A flow chart of the procedure is depicted in FIG. 7, with representative samples of dissection demonstrated in FIG. 8. The detected tumors were confirmed by histologic analysis. The data of tumor measurements are summarized in Table II:

TABLE II

Effect of Ad5CMV-p53 on tumorigenicity of H226Br in mouse model of orthotopic human lung cancer[a]

| Treatment | No. mice with Tumors/ Total Mice (%) | Mean Volume ($mm^3 \pm SD$) |
|---|---|---|
| Vehicle | 7/10 (70) | 30 ± 8.4 |
| Ad5/RSV/GL2 | 8/10 (80) | 25 ± 6.9 |
| Ad5CMV-p53 | 2/8 (25) | 8 ± 3.3[b] |

[a]Mice were inoculated with $2 \times 10^6$ H226Br cells/mouse intratracheally. On the 3rd day postinoculation, the mice were given either vehicle or viruses ($5 \times 10^7$ each in 0.1 ml) intratracheally once a day for 2 days. Tumor formation was evaluated at the end of a 6-week period.
[b]$p < 0.05$ by two-way analysis of variance when compared to the groups receiving vehicle (PBS) or virus control.

Only 25% of the Ad5CMV-p53-treated mice formed tumors, whereas in the vehicle or Ad5/RSV/GL2 control group, 70–80% of the treated mice formed tumors. The average tumor size of the Ad5CMV-p53 group was significantly smaller than those of the control groups. These results indicate that Ad5CMV-p53 can prevent H226Br from forming tumors in the mouse model of orthotopic human lung cancer.

EXAMPLE 7

Ad5CMV-p53 in Treatment Regimens

Naturally, animal models will be employed as part of the pre-clinical trials, as described herein in Examples 5 and 6.

Thereafter, patients for whom the medical indication for adenovirus-mediated gene transfer treatment has been established may be tested for the presence of antibodies directed against adenovirus. If antibodies are present and the patient has a history of allergy to either pharmacological or naturally occurring substances, application of a test dose of on the order of $10^3$ to $10^6$ recombinant adenovirus under close clinical observation would be indicated.

For the treatment of cancer using Ad5CMV-p53, recombinant adenovirus expressing p53 under the control of suitable promoter/enhancer elements, such as the CMV promoter, would be prepared and purified according to a method that would be acceptable to the Food and Drug Administration (FDA) for administration to human subjects. Such methods include, but are not limited to, cesium chloride density gradient centrifugation, followed by testing for efficacy and purity.

Two basic methods are considered to be suitable for p53 adenovirus treatment methods, a direct or local administration and a more general administration. The present methods are suitable for treating any of the variety of different cancers known to be connected with p53 mutations. In regard to general administration, a simple intravenous injection of adenovirus has been shown to be sufficient to result in viral infection of tissues at sites distant from the injection (Stratford-Perricaudet et al., 1991b), and is thus suitable for the treatment of all p53-linked malignancies. The virus may be administered to patients by means of intravenous administration in any pharmacologically acceptable solution, or as an infusion over a period of time. Generally speaking, it is believed that the effective number of functional virus particles to be administered would range from $1 \times 10^{10}$ to $5 \times 10^{12}$.

Also, particularly where lung cancer is concerned, more direct physical targeting of the recombinant adenovirus could be employed if desired, in an analogous manner to the intratracheal administration of the cystic fibrosis transmembrane conductance regulator (Rosenfeld et al., 1992). This would result in the delivery of recombinant p53 adenovirus closer to the site of the target cells.

In more detail, preferred treatment protocols may be developed along the following lines. Patients may first undergo bronchoscopy to assess the degree of obstruction. As much gross tumor as possible should be resected endoscopically. Patients should preferably undergo bronchoscopy under topical or general anesthesia. A Stifcor™ transbronchial aspiration needle (21 g) will be passed through the biopsy channel of the bronchoscope. The residual tumor site would then be injected with the p53 adenovirus in a small volume such as about 10 ml or less.

In any event, since the adenovirus employed will be replication incompetent, no deleterious effect of the virus itself on subject health is anticipated. However, patients would remain hospitalized during the treatment for at least 48 hours to monitor acute and delayed adverse reactions. Safety-related concerns of the use of replication deficient adenovirus as a gene transfer vehicle in humans have been addressed in the past (Rosenfeld et al., 1992; Jaffe et al., 1992), but the dose of adenovirus to be administered should be appropriately monitored so as to further minimize the chance of untoward side effects.

There are various criteria that one should consider as presenting the existence of a need for response or the existence of toxicity. To assist in determining the existence of toxicity, the tumor bed should be photographed prior to a course of therapy. The longest diameter and its perpendicular will be measured. Size will be reported as the product of the diameters. From these data, one can calculate from these numbers the rate of regrowth of the tumor.

The time to progression can also be measured from the first observation with reduction in tumor bulk until there is evidence of progressive disease. Progressive Disease is defined as an increase of $\geq 25\%$ in the sum of the products of the diameters of the measured lesion. Patients must have received at least two courses of therapy before a designation of progression is made. The survival of patients will be measured from entry into protocol.

Follow-up examinations would include all those routinely employed in cancer therapy, including monitoring clinical signs and taking biopsies for standard and molecular biological analysis in which the pattern of expression of various p53 genes could be assessed. This would also supply information about the number of cells that have taken up the transferred gene and about the relative promoter strength in vivo. Based on the data obtained adjustments to the treatment may be desirable. These adjustments might include adenovirus constructs that use different promoters or a change in the number of pfu injected to ensure a infection of more, or all, tumor cells without unphysiological overexpression of the recombinant genes.

It is contemplated that the expression of exogenous genes transferred in vivo by adenovirus can persist for extended periods of time. Therapeutically effective long-term expression of virally transferred exogenous genes will have to be addressed on a case by case basis. Marker genes are limited in their usefulness to assess therapeutically relevant persistence of gene expression as the expression levels required for the amelioration of any given genetic disorder might differ considerably from the level required to completely cure another disease.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. All claimed matter and methods can be made and executed without undue experimentation.

REFERENCES

The following references to the extent that they provide exemplary procedural or other details supplementary to those set forth herein, are specifically incorporated herein by reference.

Bargonetti, et al. (1991) *Cell* 65:1083–1091.
Boeheringer Mannheim Biochemicals (1992). DOTAP for high efficiency transfections, *BMBiochemica* 9(1):17.
Boshart, M. et al. (1985). A very strong enhancer is located upstream of an immediate early gene of human cytomegalovirus. *Cell*, 41:521–530.
Bishop (1987) *Science* 235:305–311.
Casey, G. Lo-Hueh, M., Lopez, M. E., Vogelstein, B., and Stanbridge, E. J. (1991). Growth suppression of human breast cancer cells by the introduction of a wild-type p53 gene. *Oncogene* 6:1791–1797.

Dai, et al. (1992) *Proc. Natl. Acad. Sci.* 89:10892–10895.
Fields et al. (1990) *Science* 249:1046–1049.
Georges et al. (1993) *Cancer Res* 53:1743–1746.
Ghosh-Choudhury and Graham (1982) Biochem. Biophys. Res. Comm. 147:964–973.
Gluzman et al., (1982) in *Eukaryotic Viral Vectors* (Gluzman, Y., Ed.) pp. 187–192, Cold Spring Harbor Press, Cold Spring Harbor, N.Y.
Graham, F. L. and A. J. van der Eb. (1973). A new technique for the assay of infectivity of human adenovirus 5 DNA. *Virology* 52:456–467.
Graham, F. L., J. Smiley, W. C. Russell and R. Nairn (1977). Characteristics of a human cell line transformed by DNA from human adenovirus type 5. *J. Gen Virol.* 36:59–72.
Grunhaus, A. and Horwitx, M. S. (1992). Adenoviruses as cloning vectors. *Semin. Virology* 3:237–2542.
Hollstein, M., Sidransky. D., Vogelstein. B., and Harris, C. (1991). p53 mutations in human cancers. *Science* 253:49–53.
Jaffe et al., (1992) *Nature Genetics* 1:372–378.
Le Gal et al., (1993) *Science* 259:988–990.
McGrory, W. J. et al. (1988). A simple technique for the rescue of early region I mutations into infectious human adenovirus type 5. *Virology* 163:614–617.
Mercer, W. E. (1992). Cell cycle regulation and the p53 tumor suppressor protein. *Critic. Rev. Eukar. Gene Express.* 2:251–263.
Mietz, et al. (1992) *EMBO* 11:5013–5020.
Montenarh, M. (1992). Biochemical, immunological, and functional aspects of the growth-suppressor/oncoprotein p53. Critic. Rev. Onco. 3:233–256.
Mulligan, (1993), *Science* 260:926.
Ragot et al., (1993) *Nature*, 361:647–650.
Rosenfeld et al., (1991) *Science*, 232:431–434.
Rosenfeld et al., (1992) *Cell* 68:143–155.
Shaw, et al., (1992) 89:4495–4499.
Spandidos, et al. (1989), *J. Pathol.*, 157:1–10.
Stratford-Perricaudet, L. and M. Perricaudet. (1991a). Gene transfer into animals: the promise of adenovirus, p. 51–61, In O. Cohen-Haguenauer and M. Boiron (Eds.), Human Gene Transfer, Editions John Libbey Eurotext, France.
Stratford-Perricaudet et al., (1991b) *Hum. Gene. Ther.* 1:241–256
Takahashi, T., Carbone, D., Takahashi, T., Nau, M. M., Hida, T., Linnoila, I., Ueda, R., and Minna, J. D. (1992). Wild-type but not mutant p53 suppresses the growth of human lung cancer cells bearing multiple genetic lesions. 1992. *Cancer Res.* 52:2340–2342.
Tooza, J. (1981). Molecular biology of DNA Tumor viruses, 2nd ed. Cold Spring Harbor Laboratory, Cold Spring Harbor, N.Y.
Travali, et al. (1990), *FASEB*, 4:3209–3214.
Yonish, et al. (1991), *Nature* 352:345–347.
Weinberg, R. A. (1991). Tumor suppressor gene. *Science* 254:1138–1145.
Wilcock, et al. (1991) *Nature* 349:429–431.
Zakut-Houri et al. (1985), *EMBO J.*, 4:1251–1255.
Zhang, et al. (1993) *BioTechniques* in press.

---

What is claimed is:

1. A recombinant adenovirus which carries an adenovirus vector construct comprising an expression region encoding p53 under the control of a cytomegalovirus IE promoter.

2. The recombinant adenovirus of claim 1, wherein said vector construct further comprises a polyadenylation signal.

3. The recombinant adenovirus of claim 1, wherein said recombinant adenovirus is replication deficient.

4. The recombinant adenovirus of claim 1, wherein said vector construct lacks the E1A and E1B regions.

5. The recombinant adenovirus of claim 3, wherein said expression region replaces said E1A and E1B regions of said vector construct.

6. The recombinant adenovirus of claim 5, wherein said adenovirus has the genome structure of FIG. 1.

7. A recombinant host cell infected with a recombinant adenovirus which carries an adenovirus vector construct comprising an expression region encoding p53 under the control of a cytomegalovirus IE promoter.

8. An adenovirus vector construct comprising an expression region encoding p53 under control of a cytomegalovirus IE promoter.

9. The adenovirus vector construct of claim 8, further comprising a polyadenylation signal.

10. The adenovirus vector construct of claim 8, wherein said vector construct is replication deficient.

11. The adenovirus vector construct of claim 10, wherein said vector construct lacks the E1A and E1B regions.

12. The adenovirus vector construct of claim 11, wherein said expression region replaces said E1A and E1B regions of said vector construct.

13. The adenovirus vector construct of claim 12, wherein said vector construct has the genome structure of FIG. 1.

* * * * *

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 19
      (B) TYPE: Nucleic acid
      (C) STRANDEDNESS: Single
      (D) TOPOLOGY: Linear (ii) MOLECULE TYPE: <Unknown>

(xi) SEQUENCE DESCRIPTION: SEQ ID NO: 1:

GGCCCACCCC CTTGGCTTC                                19

(2) INFORMATION FOR SEQ ID NO: 2:

(i) SEQUENCE CHARACTERISTICS:
      (A) LENGTH: 20
      (B) TYPE: Nucleic acid
      (C) STRANDEDNESS: Single
      (D) TOPOLOGY: Linear (ii) MOLECULE TYPE: <Unknown>

(xi) SEQUENCE DESCRIPTION: SEQ ID NO: 2:

TTGTAACCAT TATAAGCTGC                               20

(2) INFORMATION FOR SEQ ID NO: 3:

```
    (i) SEQUENCE CHARACTERISTICS:
        (A) LENGTH: 20
        (B) TYPE: Nucleic acid
        (C) STRANDEDNESS: Single
        (D) TOPOLOGY: Linear (ii) MOLECULE TYPE: <Unknown>

(xi) SEQUENCE DESCRIPTION: SEQ ID NO: 3:

TCGTTTCTCA GCAGCTGTTG                                                    20

(2) INFORMATION FOR SEQ ID NO: 4:

(i) SEQUENCE CHARACTERISTICS:
        (A) LENGTH: 20
        (B) TYPE: Nucleic acid
        (C) STRANDEDNESS: Single
        (D) TOPOLOGY: Linear (ii) MOLECULE TYPE: <Unknown>

(xi) SEQUENCE DESCRIPTION: SEQ ID NO: 4:

CATCTGAACT CAAAGCGTGG                                                    20
```